(12) United States Patent
Herskovic

(10) Patent No.: US 10,335,559 B2
(45) Date of Patent: Jul. 2, 2019

(54) COMBINED LARYNO-TRACHEAL ANESTHETIC AND STYLET DEVICE

(71) Applicant: Joshua J. Herskovic, Highland Park, IL (US)

(72) Inventor: Joshua J. Herskovic, Highland Park, IL (US)

( * ) Notice: Subject to any disclaimer, the term of this patent is extended or adjusted under 35 U.S.C. 154(b) by 343 days.

(21) Appl. No.: 15/368,915

(22) Filed: Dec. 5, 2016

(65) Prior Publication Data

US 2017/0106159 A1    Apr. 20, 2017

Related U.S. Application Data

(62) Division of application No. 14/301,170, filed on Jun. 10, 2014, now Pat. No. 9,539,402.

(60) Provisional application No. 61/832,979, filed on Jun. 10, 2013.

(51) Int. Cl.
| | | |
|---|---|---|
| *A61M 11/00* | (2006.01) | |
| *A61M 16/04* | (2006.01) | |
| *A61M 19/00* | (2006.01) | |
| *A61M 5/168* | (2006.01) | |
| *A61M 5/145* | (2006.01) | |
| *A61M 39/24* | (2006.01) | |
| *A61B 1/267* | (2006.01) | |

(52) U.S. Cl.
CPC .......... *A61M 11/007* (2014.02); *A61M 5/145* (2013.01); *A61M 5/16881* (2013.01); *A61M 16/0463* (2013.01); *A61M 16/0488* (2013.01); *A61M 19/00* (2013.01); *A61M 39/24* (2013.01); *A61B 1/267* (2013.01); *A61M 16/04* (2013.01); *A61M 2205/3375* (2013.01); *A61M 2205/3592* (2013.01)

(58) Field of Classification Search
CPC ............... A61M 11/006–11/007; A61M 16/04
See application file for complete search history.

(56) References Cited

U.S. PATENT DOCUMENTS

| | | | |
|---|---|---|---|
| 9,539,402 B2 * | 1/2017 | Herskovic | A61M 16/0463 |
| 2008/0210243 A1 * | 9/2008 | Clayton | A61M 16/04 128/207.15 |
| 2012/0184921 A1 * | 7/2012 | Brillant | A61M 16/04 604/239 |
| 2013/0277443 A1 * | 10/2013 | Croll | A61M 11/06 239/1 |
| 2014/0018616 A1 * | 1/2014 | Melsheimer | A61M 16/04 600/104 |

* cited by examiner

*Primary Examiner* — Kristen Matter

(57) ABSTRACT

A device for delivering medication is presented. The device has a conduit with an upstream end and a downstream end. The downstream end of the conduit delivers the medication. The device has a housing with an open end and an end forming a flat substrate. The housing receives a syringe containing medication and having a plunger. The device also has mechanism for releasing the medication from the syringe and a mechanism for pressurizing the medication. The device has a connector from providing a connection between the syringe and the upstream end of the conduit.

8 Claims, 28 Drawing Sheets

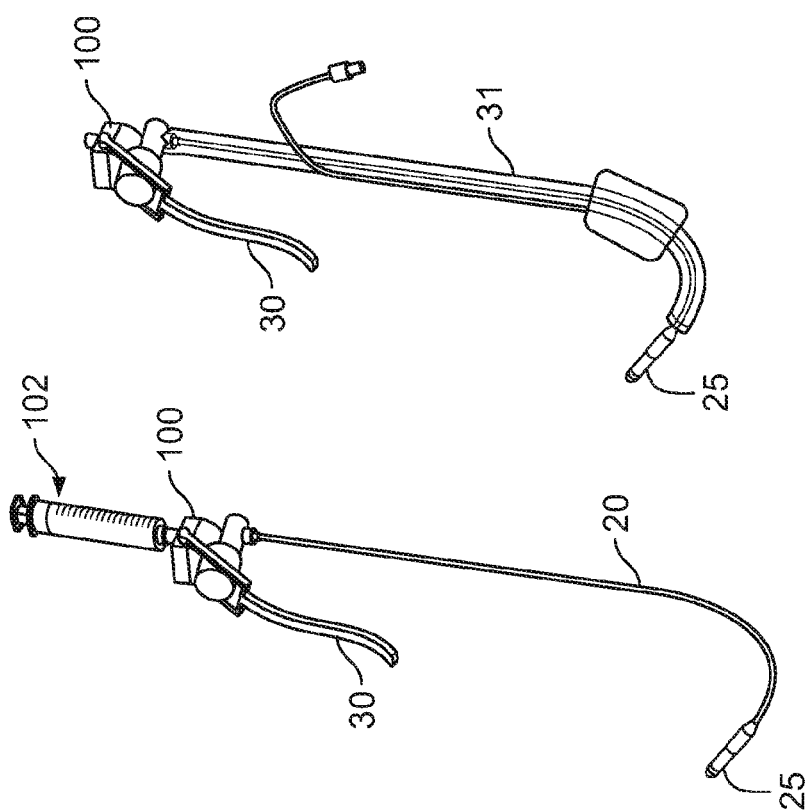
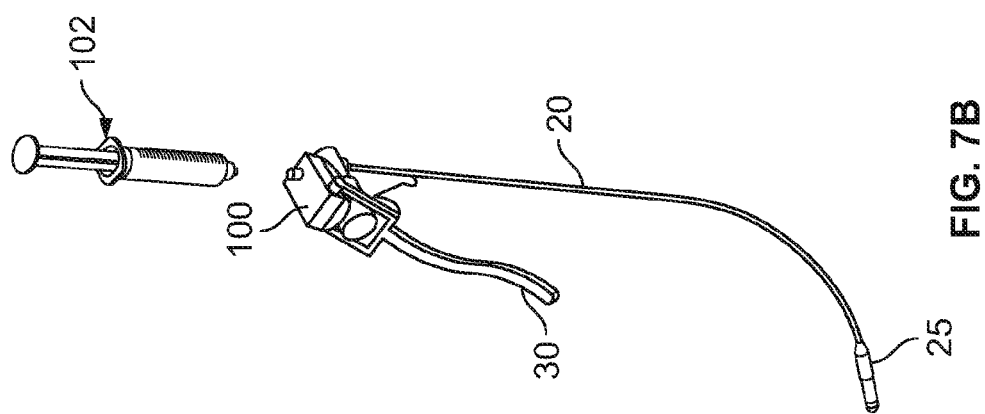
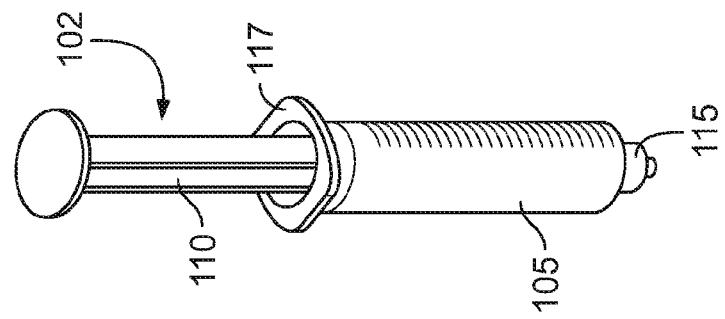
FIG. 7A  FIG. 7B  FIG. 7C  FIG. 7D

COMBINED LARYNO-TRACHEAL ANESTHETIC AND STYLET DEVICE

PRIORITY

This utility application is a divisional application of U.S. patent application Ser. No. 14/301,170, filed on Jun. 10, 2014, now U.S. Pat. No. 9,539,402, which claims the benefit of U.S. Provisional Patent Application No. 61/832,979, filed on Jun. 10, 2013, the entirety of both applications are hereby incorporated by reference.

BACKGROUND

1. Field of the Invention

The present invention relates to a method and device for anesthetizing and intubating, and more particularly, the present invention relates to a method and device for anesthetizing and intubating a patient with a single hand movement.

2. Background

Laryngo-tracheal anesthesia (LTA) is an important component of the anesthetic plan for general anesthesia during surgery. LTA blunts airway reflexes and discomfort involved in the manipulation of the airway for surgery and facilitates placement and maintenance of an endotracheal tube (ETT). Of the approximately 15 million general anesthetic procedures performed each year that require an ETT, about one third will require the use of LTA.

Often laryngo-tracheal anesthetic is applied just prior to placement of the endotracheal tube. Typically, the anesthetist visualizes the vocal cords by direct laryngoscopy, places a cannula connected to a syringe containing a local anesthetic thru the vocal cords, and sprays the local anesthetic within the trachea and oropharynx. In a second direct laryngoscopy, the anesthetist places the endotracheal tube through the vocal cords and into the trachea by sliding the ETT over a wire (here, commonly referred to as a stylet) or, in some cases an introducer.

These two or more discreet steps potentially distract the anesthetist who must first reach for the LTA device and then the ETT. Also, the act of direct laryngoscopy places a great deal of stress on the patient. Placement of the laryngoscope blade on or near the epiglottis causes exaggerated sympathetic reflexes (and concomitant blood pressure swings) because of the extreme nerve sensitivity in this area. Many patients, such as those with heart disease, do not tolerate these large swings in blood pressure and in heart rate which can occur with multiple acts of direct laryngoscopy.

Additionally, prolonged direct laryngoscopy creates increased risks for the patient. The best view of the vocal cords is obtained on the first attempted direct laryngoscopy. Prolonging direct laryngoscopy causes increased edema, tissue trauma, bleeding, and secretions, which all impair the view of the vocal cords by the time the ETT is to be placed. The actual injection of the LTA liquid also obscures the view. During this time period, the trachea is unprotected and the risk of aspiration is increased. Also, on occasion the stimulation caused by LTA placement in an incompletely paralyzed patient may cause reflexive spasm of the vocal cords, thus preventing placement of the ETT altogether.

Often a "top heavy" intubation device, when loaded into an endotracheal tube inadvertently causes trauma to the eyes and face of the patient during manipulation of the device.

Attempts have been made to administer LTA through an ETT. However, these devices require extreme dexterity as the anesthesiologist must change hand positions multiple times to inject the LTA and place the ETT. For example, the anesthesiologist uses one hand position to initially access the vocal cords, another hand position to dispense anesthesia, and yet another hand position to advance the ETT. Changing hand positions is further complicated because the anesthesiologist must dedicate one hand to holding the laryngoscope blade. Therefore the intended benefit of decreased direct laryngoscopy time and a less traumatic experience to the patient is largely lost. In fact, the greatest challenge of such a combined stylet and LTA device is to be able to perform the intended function of LTA application without increasing the current level of difficulty, dexterity, and skill needed to administer the LTA, all without increase movement of the device in situ.

A need exists in the art for a method and system to allow for injection of local anesthetic while still holding an ETT in the proper position for intubation. The method and device should decrease the difficulty of intubating patients by acting as an introducer or "bougie." Further still, the device should not add much weight and bulk to the top of the endotracheal tube.

SUMMARY

An object of the present invention is to improve upon the limitations of prior art LTA devices.

Another object of the present invention is to provide an LTA device that also serves as a stylet and introducer during intubation procedures. A feature of the present invention is that the LTA device has a malleable conduit that can be bent and that can maintain its shape to guide an ETT during intubation. An additional feature is that pre-shaped conduits can also be used with the invented device. Another feature of the present invention is that the end nozzle of the LTA device extends past the end of the ETT and acts as an introducer. An advantage of the present invention is that the devices used to administer anesthetic and guide the ETT are combined into a single device that can be used while the ETT is being placed.

Still another objection of the present invention is to provide an LTA device that can be used during ETT placement without increasing the requisite skill and dexterity of operation. A feature of the present invention is a physical activation means such as lever, trigger, button, or a non-physical activation means (such as an audio or electronic cue) that causes anesthetic or other medicament to exit a reservoir, that physical activation means placed near the region of the device adapted to be grasped by the user's hand. An advantage of the invention is that the device allows the anesthesiologist to deliver doses of anesthetic during an intubation procedure without needing to change hand position.

Still another object of the present invention is to provide a method to decrease the total time involved in performing a direct laryngoscopy. A feature of the present invention is utilizing an LTA device that functions as both a means for anesthetizing a patient's trachea and posterior pharynx and also as a stylet and introducer for placing an ETT. An advantage of the present invention is that separate direct laryngoscopies do not have to be performed for LTA and ETT placement; instead the method combines both functions such that they are performed simultaneously or within a few seconds, approximately one to 10 seconds, and preferably within about 3-6 seconds, and most preferably less than 5 seconds, from each other. A further advantage is that the potential injuries to and stress on the patient from repeated procedures are eliminated. A still further advantage is that the liability exposure for the anesthesiologist is consequently reduced.

A further object of the present invention is to provide an LTA device that is modular in design. A feature of some embodiments of the present invention is that the malleable conduit, dispenser, and anesthetic cartridges can be easily assembled using luer linkages. An advantage of the present invention is that components can be replaced or sterilized as needed without the need to replace the entire device. Alternatively, the entire device can be made disposable. Another advantage of the present invention is that the same introducer or dispenser system can be used on two different LTA medical device designs, and even as a device for administering medicaments in non-intubation scenarios. This allows for lower manufacturing costs and decreased hospital investment in two platforms.

Briefly, the invention provides a laryngo-tracheal anesthetic device, said device comprising a conduit with a first end and a second end, wherein the second end is designed to enter a patient, a means for pressurizing anesthetic, wherein said means is adapted to receive a cartridge of anesthetic, a means for releasing anesthetic from the reservoir into the malleable tube; and a nozzle at the second end of the malleable tube.

The invention also provides a device for pressurizing a cartridge of anesthetic on an intravenous line, the device comprising a housing with a first end and a second end, wherein the housing's first end is open and the housing's second end is a flat substrate and wherein the housing is adapted to receive a vial of anesthetic, said vial being plugged with a stopper; a piston extending from the flat substrate, wherein the piston exerts pressure on the vial stopper; a needle that punctures the stopper and provides fluid communication to the interior of the vial, and wherein the needle defines a channel through the piston and through the flat substrate; a luer connection in fluid communication with the channel defined by the needle; and a variable flow regulator in fluid communication with the luer connection, wherein the variable flow regulator is designed to receive an intravenous conduit.

BRIEF DESCRIPTION OF THE DRAWINGS

The invention together with the above and other objects and advantages will be best understood from the following detailed description of the preferred embodiment of the invention shown in the accompanying drawings, wherein:

FIG. 7A-D depict a syringe embodiment of the LTA device, in accordance with the features of the present invention;

DETAILED DESCRIPTION

The foregoing summary, as well as the following detailed description of certain embodiments of the present invention, will be better understood when read in conjunction with the appended drawings.

As used herein, an element step recited in the singular and preceded with the word "a" or "an" should be understood as not excluding plural said elements or steps, unless such exclusion is explicitly stated. Furthermore, the references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

The present invention is a device for administering medicaments, such as laryngo-tracheal anesthetic. The invention provides a device and method for administering medicaments in hard to reach places, such as lumens.

Figure 1:
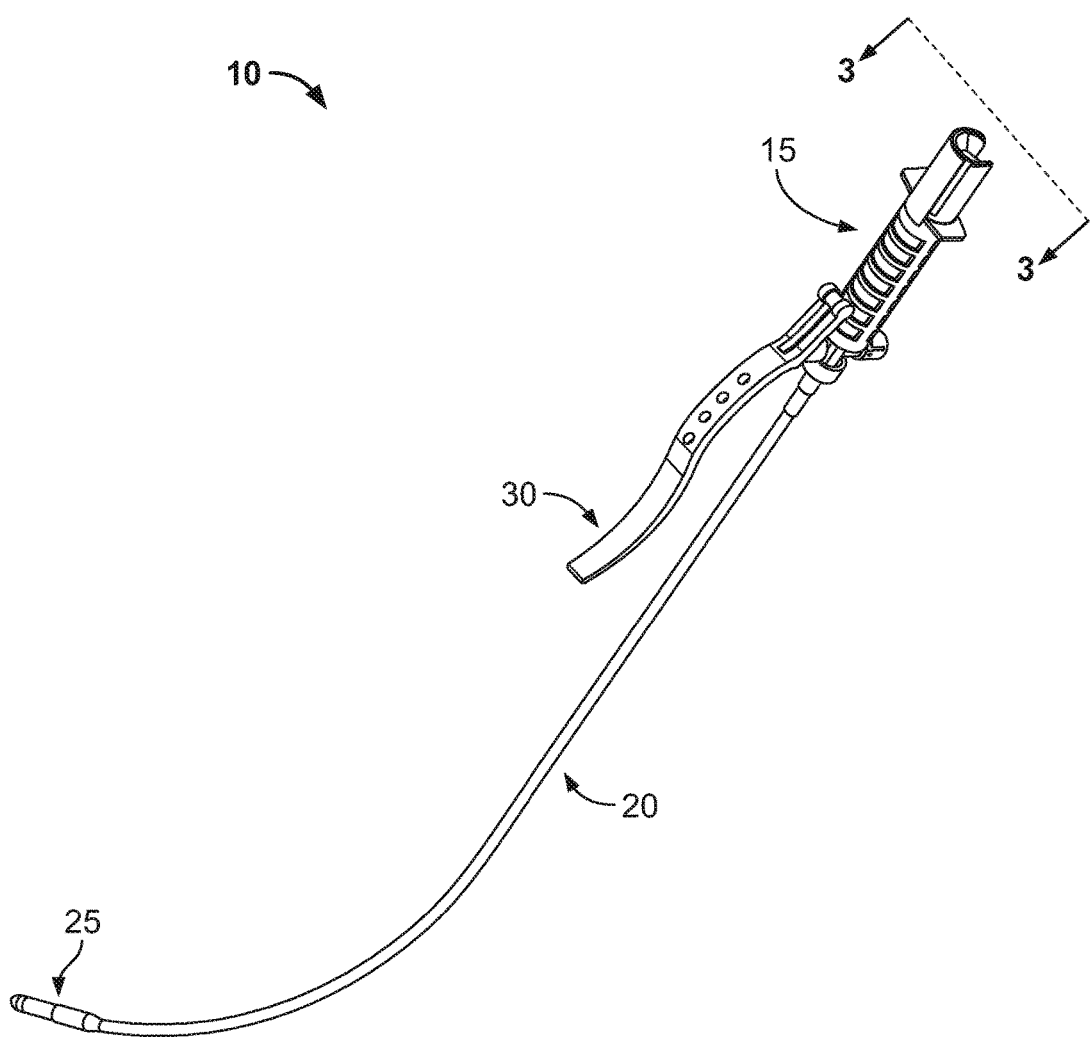
FIG. 1 is a depiction of a vial embodiment of the LTA device, in accordance with the features of the present invention.

As depicted in FIG. 1, the LTA device 10 defines an elongated body generally comprised of a dispenser 15 in fluid communication with a conduit 20. A distal end of the conduit terminates in a nozzle 25. The dispenser 15 dispenses anesthetic through the conduit 20 and out of the nozzle 25 upon actuation via an actuation means 30. The actuation means 30 is positioned intermediate of the dispenser 15 and the nozzle 25. The actuation means in the embodiment shown is in pivotal communication with a distal end of the dispenser. In an embodiment of the invention, the longitudinal axis of each of the dispenser, the conduit, and the nozzle are coaxial.

Figure 2:
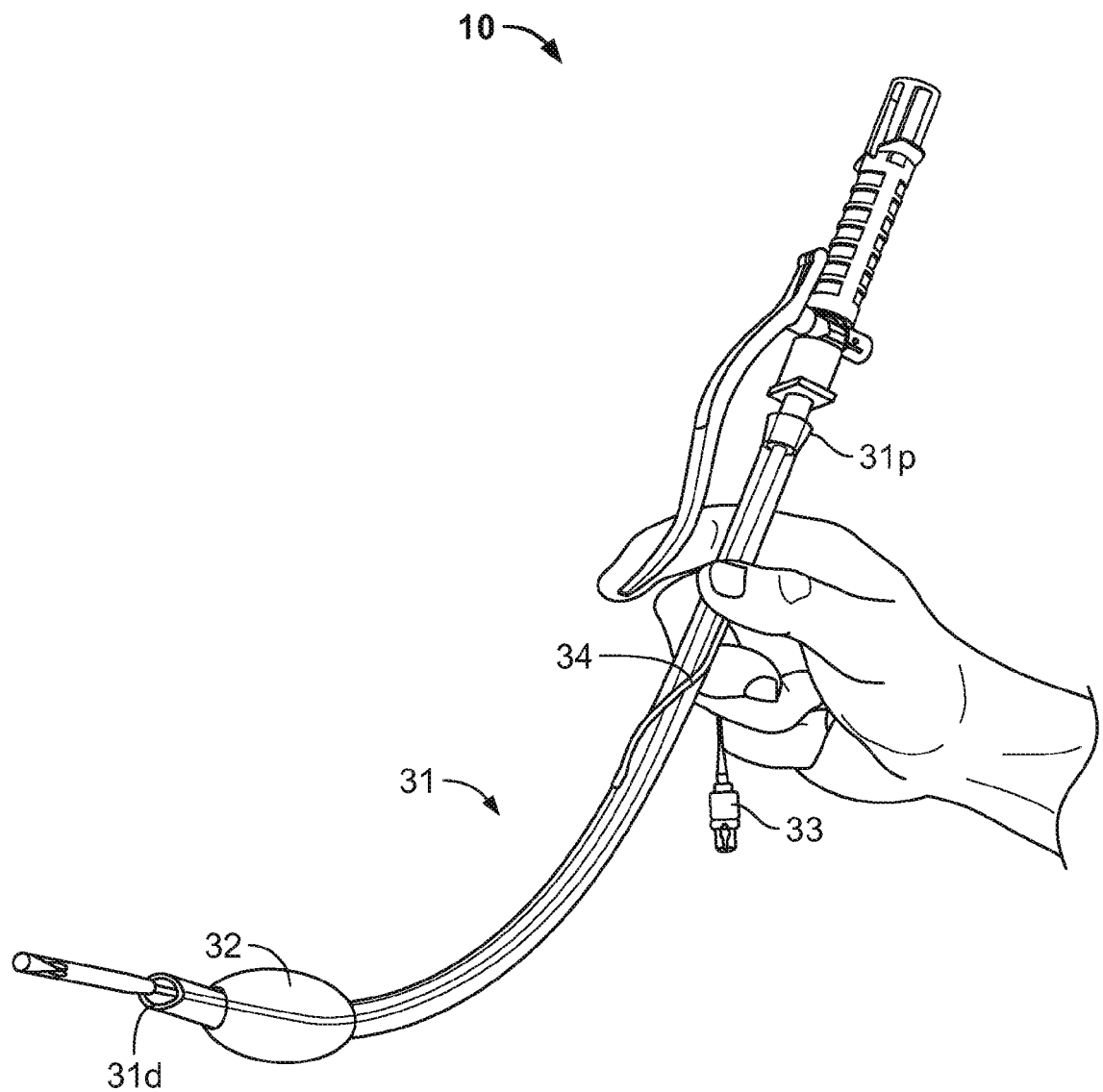
FIG. 2 is a depiction of the device of FIG. 1 as held in the proper position by an anesthesiologist.

The LTA device not only provides anesthetic during an intubation procedure, but it also acts as a tool to aid in placement of the ETT and more generally as means to direct applications of medicaments. Accordingly, FIG. 2 depicts in phantom the LTA device 10 substantially enclosed inside of (or substantially encapsulated by) an ETT 31 prior to intubation. The ETT 31 is generally comprised of a proximal end 31$p$, a distal end 31$d$, a balloon cuff 32 near the distal end 31$d$, a cuff inflator 33, and a pilot tube 34. The balloon cuff 32 expands in the trachea to stabilize the ETT and prevent aspiration. The cuff inflator 33 is pumped or otherwise actuated to force air into the cuff 32 through the pilot tube 34. In placing the LTA device 10 in the ETT 31, the malleable conduit 20 functions as a stylet such that it can be reversibly shaped to aid in the placement of the endotracheal tube. Further, the nozzle 25 extends past the end of the endotracheal tube and functions as a bougie, or introducer, in that it can guide the LTA device 10 and ETT 31 past the patient's epiglottis and glottis during intubation.

The LTA device 10 allows the anesthesiologist to provide these functions while also maintaining the level of skill and dexterity of a normal intubation procedure. For example, an anesthesiologist can administer a dose of anesthetic without having to move his hands from the proper hand position as depicted in FIG. 2. In this position, the anesthesiologist positions the device between his thumb and forefinger such that the device is supported by the middle phalange of the forefinger and the distal phalange of the second or middle finger. The anesthetic dispensing actuation means such as the lever shown in FIG. 1 is actuated by the distal phalange of the forefinger. Furthermore, after completion of intubation, the actuation means, or lever, provides the additional function of aiding in removal of the stylet and introducer device from the ETT. The lever provides leverage against the static frictional forces between the stylet and the ETT to facilitate removal of the stylet from the ETT.

Dispenser Detail—
Vial Embodiment

The dispenser 15 comes in a variety of embodiments. In each embodiment, the dispenser 15 is adapted to receive a cartridge or ampule of anesthetic. The dispenser 15 releases the contents of the cartridge for dispersion through the conduit 20 and out the nozzle 25 when actuated by the actuation means 30. However, the means for pressurizing the contents and the actuation means varies between the following embodiments.

Figure 3A:
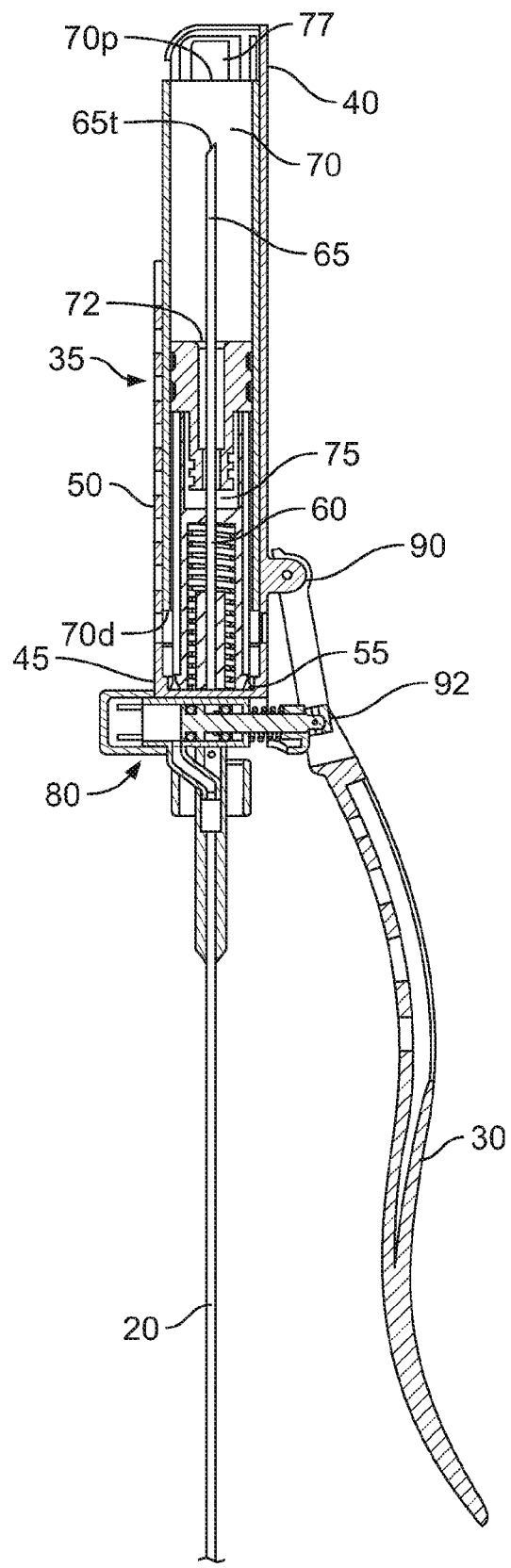
FIG. 3A is a sectional view of the dispenser portion of the device, taken along line 3-3 of FIG. 1.

In a primary embodiment that can be seen in FIG. 3, the dispenser 15 is comprised of a housing 35 defined by a first (or proximal) end 40, a second end 45, and a longitudinally extending perimeter wall 50. Towards the second end 45 is a flat substrate 55. Extending proximally from the flat substrate 55 is a piston 60. The piston can be spring loaded or hydraulically-, pneumatically-, or electrically-actuated. Various embodiments of the piston are discussed in greater detail infra. In a preferred embodiment, the piston 60 is spring loaded. Extending coaxial with and proximal from the piston 60 is a needle 65, such that the needle extends toward the first end 40 of the housing. The needle 65 defines a fluid passageway that extends from the tip of the needle 65$t$, through the piston 60, and through the first substrate 55. This fluid passageway is in fluid communication with the interior cavity defined by the conduit 20.

In operation, the user provides a cartridge of anesthetic, which, in this embodiment, is a vial 70 with a stopper 72.

Figure 4A:
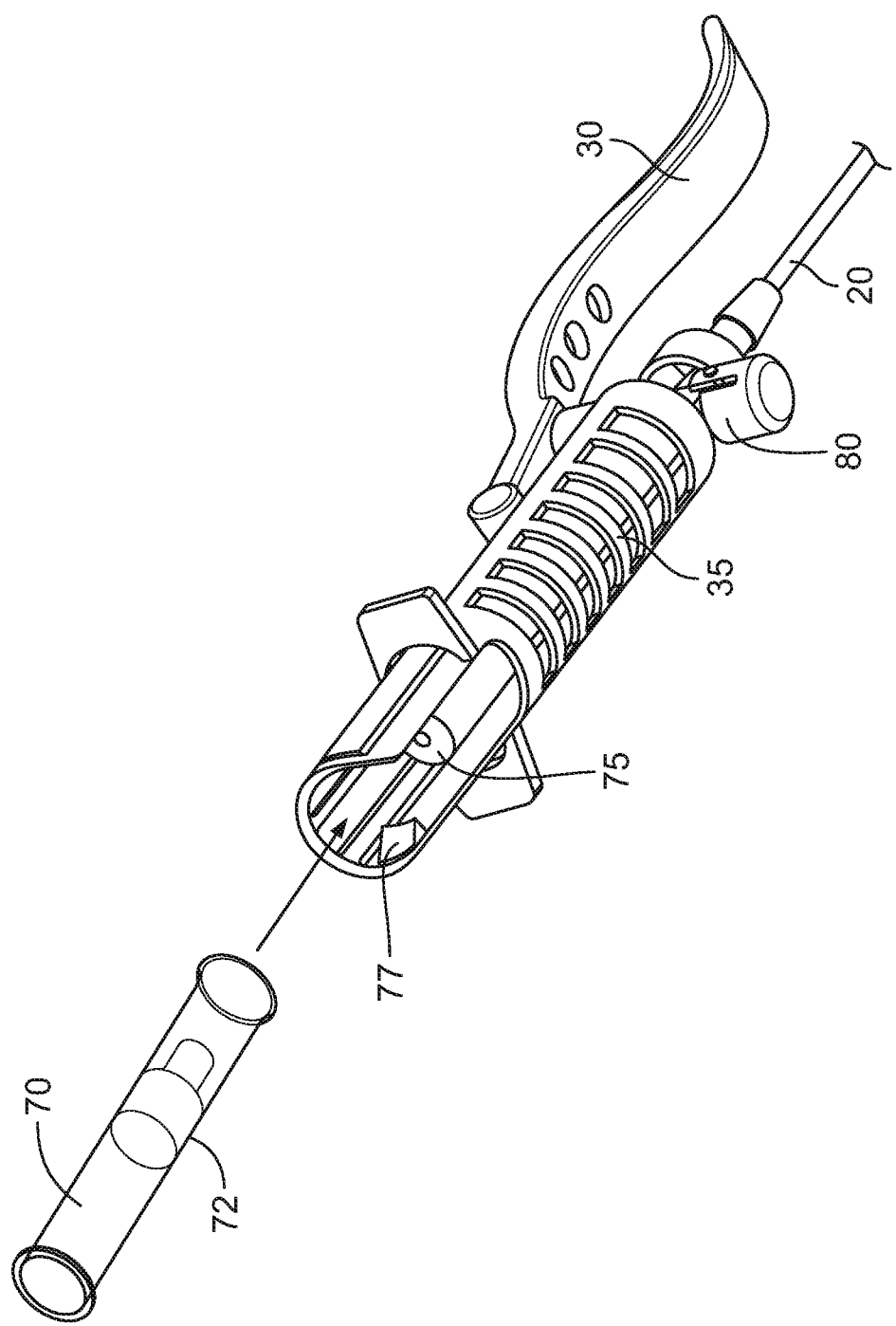
FIGS. 4A-B depict a vial being loaded into the device of FIG. 1, in accordance with features of the present invention.
Figure 4B:
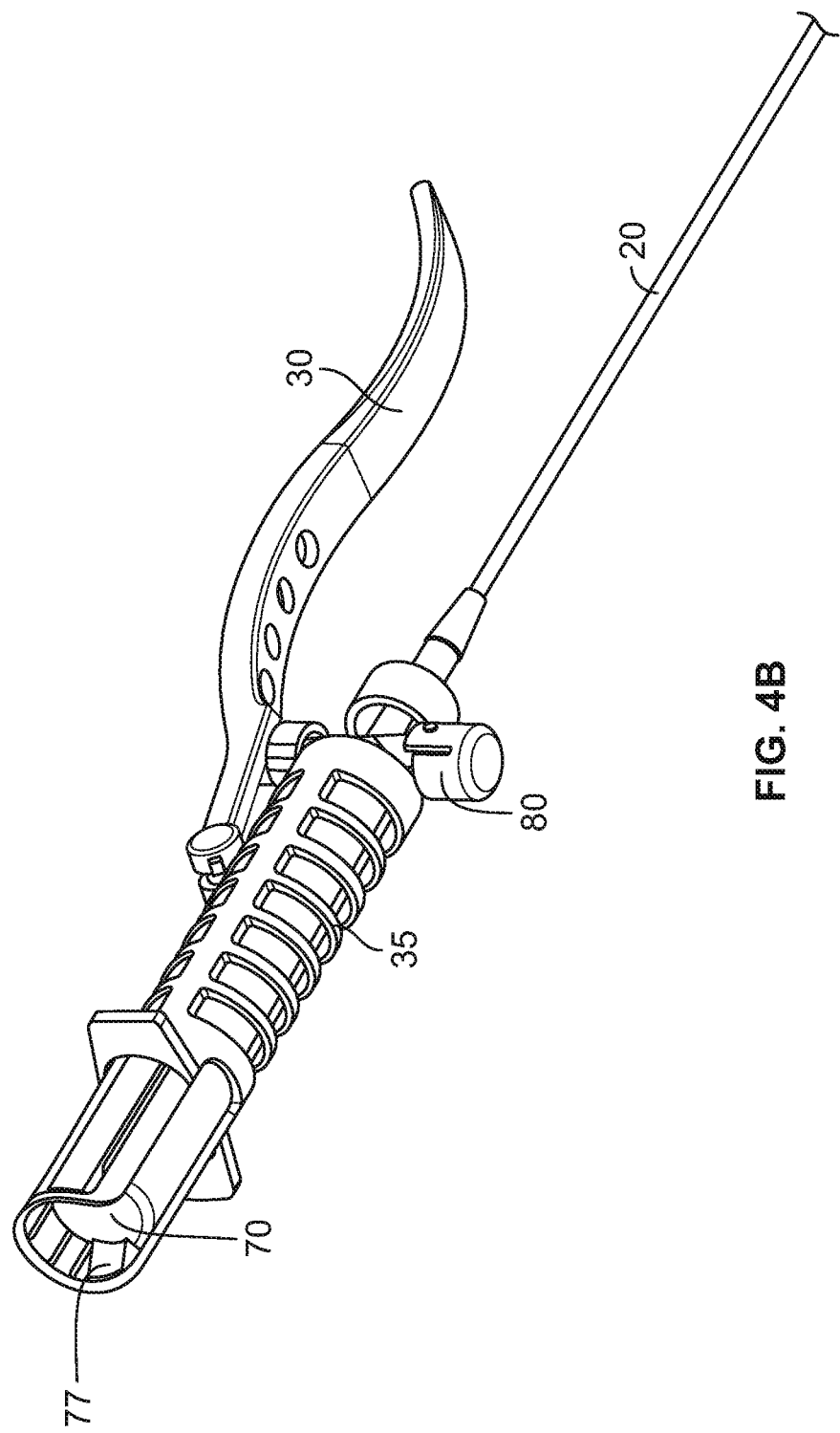

The process of loading the vial 70 is depicted in FIGS. 4A-B. Cross sections of the vial 70 and the housing 35 are such that the housing is adapted to slidably receive the vial, whereby the longitudinal axis of the housing and the vial are collinear. The user loads the vial 70 into the housing 35, sliding vial 70 in the direction of the flat substrate 55 as shown by the arrow in FIG. 4A. Under pressure applied by the user, the needle 65 punctures the stopper 72, thereby providing fluid communication between the LTA device 10 and the contents of the vial 70. As the user continues to apply pressure to the vial 70, the stopper 72 contacts the piston 60, driving the piston head 75 towards the flat substrate 55. The vial 70 is then locked into place via a tab 77 or cap at the first end 40 of the housing 35. Once the tab 77 engages the vial 70, the user ceases applying pressure to the vial 70. A small space separates the distal end 70$d$ of the vial 70 from the flat substrate 55 so as to provide room for compression of the piston 60, especially when the piston 60 is spring loaded.

The tab 77 is a tapered projection that terminates in a hook; this allows the vial 70 to be slid past while loading but prevents the vial 70 from slipping out of the housing 35 under the force of the piston 60. In one embodiment, the tab 77 is a cantilever snap fit joint. Insertion of the vial 70 creates a flexural load on the projection until the vial slides past the hook and catches on the depression under the hook. At this point the projection returns to a near stress free condition while preventing backward movement of the medication vial.

Upon loading, the contents of the vial 70 become pressurized as a result of the pressure exerted by the compressed piston 60. The piston 60 exerts a positive pressure on the stopper 72, which, in turn, exerts pressure on the contents of the vial 70. The pressurized contents are expelled through the needle 65, which is in fluid communication with conduit 20, but not yet allowed to flow through the conduit. When the contents are allowed to be expelled, the fluid pressure on the stopper 72, opposing the piston 60, is lessened, and the piston 60 extends away from the flat substrate 55, causing the stopper 72 to move towards the proximal end 70$p$ of the vial 70. Thus, the piston 60 exerts continuous positive pressure on the contents of the vial 70.

Intermediate of the flat substrate 55 and the conduit 20 is a valve 80. The valve 80 is in mechanical communication with the actuation means 30. As depicted in FIG. 1, the actuation means 30 is a depending lever, button, trigger or audio cue which actuates the device remotely via blue tooth, infrared, radio frequency or other electronic conveyance. When the user engages the actuation means 30, the valve 80 is opened, and the contents of the vial 70 can flow through the needle 65 into the conduit 20.

Figure 3C:
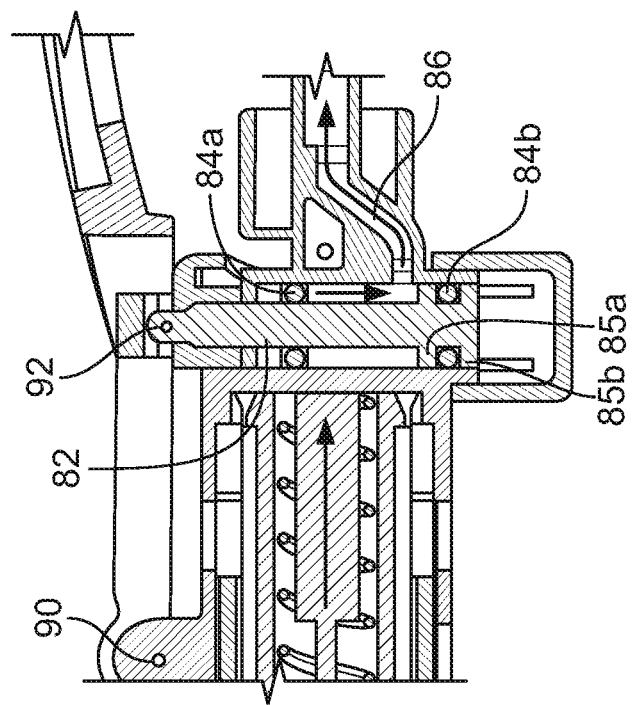
FIGS. 3B-C depict detail views of a valve, in accordance with features of the present invention.
Figure 3B:
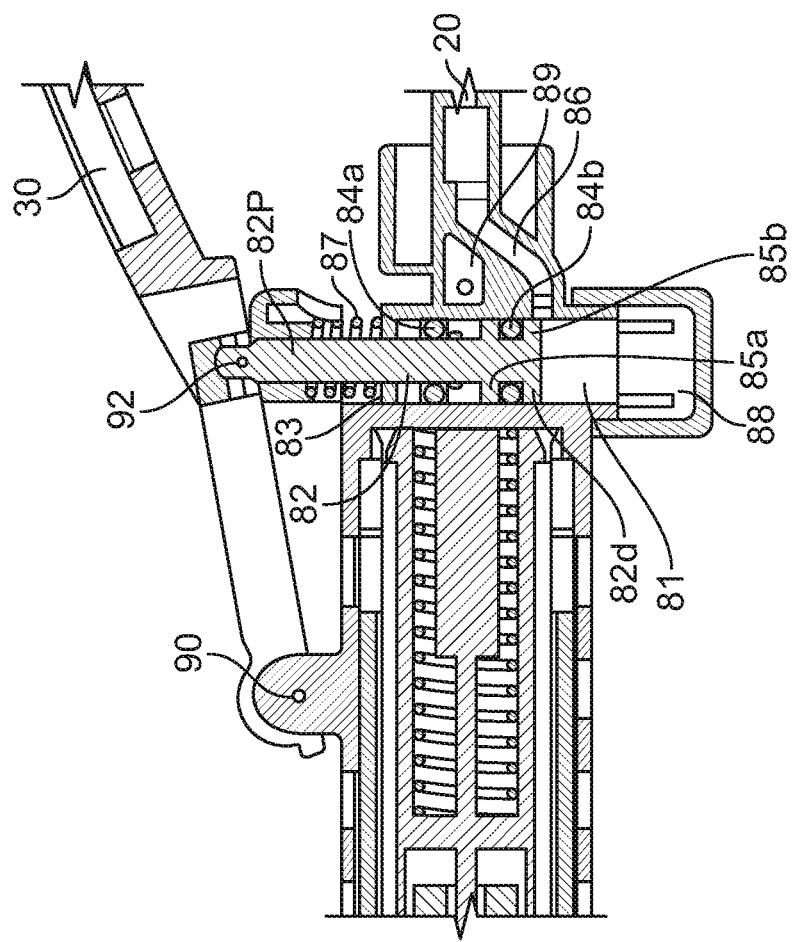

FIG. 3B depicts a sectional view of the valve 80. The valve 80 defines a valve cavity 81, which houses a valve plunger 82. The valve plunger 82 has a proximal end 82$p$ and a distal end 82$d$, and the proximal end 82$p$ is in mechanical communication with the actuation means 30. The valve plunger 82 is slidably received into the valve cavity 81 through aperture 83. Fluid is prevented from escaping the valve cavity by a first O-ring 84$a$. The distal end 82$d$ of the valve plunger 82 contains two flanges 85$a$, 85$b$ that sandwich a second O-ring 84$b$. The flanges 85$a$, 85$b$ and second O-ring 84$b$ have a diameter such that they block fluid flow to the downstream portion of the valve cavity 81. The downstream portion of the valve cavity 81 contains an outlet 86, which is in fluid communication with the conduit 20.

As can be seen in FIG. 3B, prior to actuation, the valve 80 blocks fluid flow between the needle 65 and the outlet 86. As shown in FIG. 3C, actuation causes the flanges 85a, 85b and second O-ring 84b to slid past the outlet 86, thereby allowing fluid communication between the needle 65 and the conduit 20 as demonstrated with the flow arrows. When the user removes pressure from the actuation means 30, the plunger is pulled back into its initial position by a spring 87. A valve cap 88 is placed at the end of the valve opposite to the spring 87. The valve cap 88 prevents fluid from the valve from escaping. Other blocks, plugs, or impediments could also be used to stem flow from inside the valve.

Because of the positioning of the outlet 86, the outlet is bent at an approximately 45.degree. angle to establish communication between the needle 65 and the conduit. The region 89 proximal to the outlet 86 does not provide fluid communication with the conduit. The main purpose of this region 89 is to provide a larger diameter upon which to affix the ETT. The region 89 also improves the feel of stability in the anesthesiologist's hand.

FIG. 1 shows the actuation means 30, which is a lever or trigger. As depicted in FIG. 3, the actuation means 30 terminates at is proximal end in a fulcrum point 90 which is in rotatable communication with an exterior surface of the dispenser housing 35. Spatially disposed of the fulcrum point 90, and in distal relation therefore on the actuation means 30 is a valve actuation point 92 comprising a rigid substrate 82 (hereinafter referred to as a valve plunger) positioned at approximately 90 degrees from the longitudinal axis of the housing. The plunger 82 has a first end rotatably attached to the actuation means 30 and a second end medially protruding and contacting the valve 80. There, the valve plunger 82 in the valve 80 connects to the actuation means 30. In this way, when the user applies medially directed force to the actuation means 30, the valve plunger 82 is depressed and the valve is opened. As long as the user continues to apply force to the actuation means, the LTA device 10 will provide a spray of anesthetic mist.

Figure 5C:
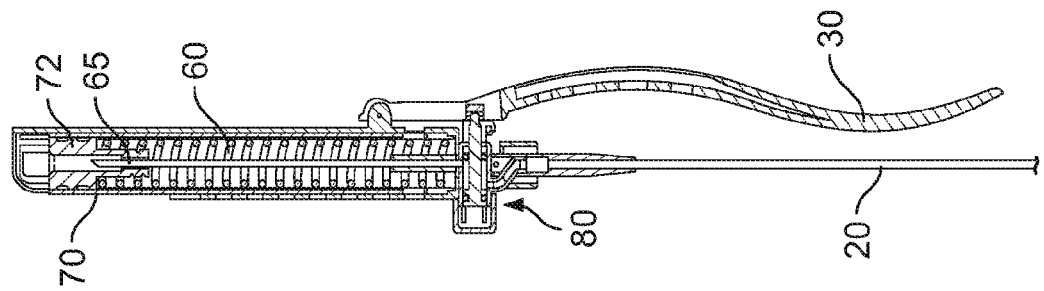
FIGS. 5A-C depict a vial embodiment in which the piston is inside the vial, in accordance with features of the present invention.
Figure 5B:
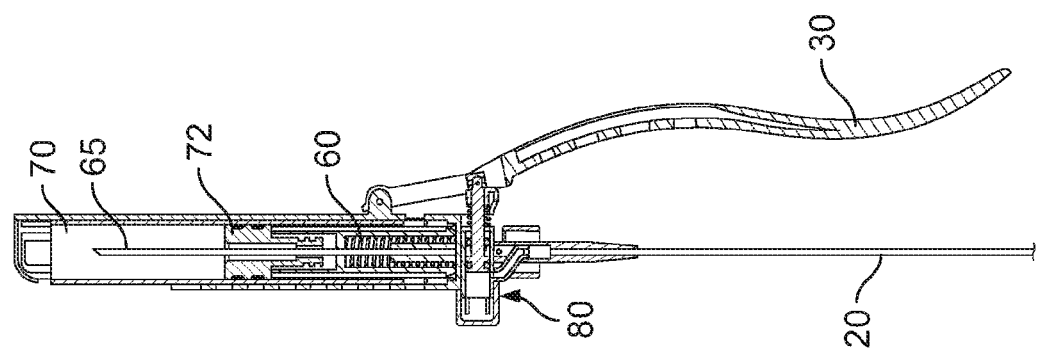
Figure 5A:
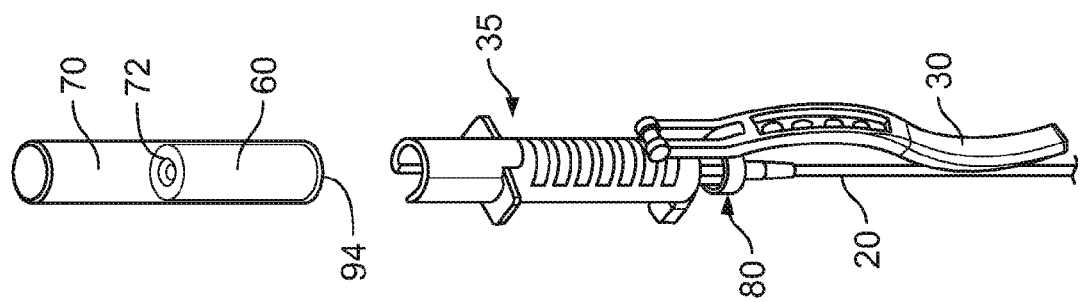

In another embodiment, the piston 60 is not located in the housing 35. Instead the piston is located in the vial 70, as shown in FIG. 5A. The distal end 70d of the vial 70 has a cap 94 that contains the liquid and piston 60 inside the vial. The piston 60 is compression spring mounted to the cap 94. The rubber stopper 72 defines the piston head. Additionally, the cap 94 is preferably pierceable such that the needle 65 in the housing can puncture the cap 94 during insertion and filling of the vial. As liquid is added to the vial, the pressure of the fluid pushes the piston in a distal direction 60 towards the cap 94. As the fluids are dispensed from the vial 70, the piston 60 exerts a continuous positive pressure on the fluids, maintaining pressurization. FIG. 5B shows this embodiment when the vial is first loaded. As can be seen, the spring is completely compressed. FIG. 5C depicts the vial when empty, wherein the piston is fully extended.

As mentioned supra, the piston 60 can also be pneumatically, hydraulically, or electrically actuated. For instance, the piston 60 can be the magnetic shaft of a linear shaft motor. The piston 60 could also be a pneumatic actuator. The device 10 would require compressed air for operation, but medical air compressors are commonly available, especially for use in dental offices. Additionally, the piston could be the cylinder rod of a hydraulic cylinder. Similar to the pneumatic embodiment, the hydraulic embodiment would require a reservoir of hydraulic fluid and a pump for operation; nevertheless, these items are commonly available in a variety of sizes and for a variety of applications. The valve plunger 82 can also be pneumatically, hydraulically, or electrically actuated. Such devices as linear motors, solenoid valves, pneumatic actuators, and hydraulic cylinders could drive the plunger 82, pushing the flanges 85a, 85b and second O-ring 84a past the outlet 86.

Figure 6A:
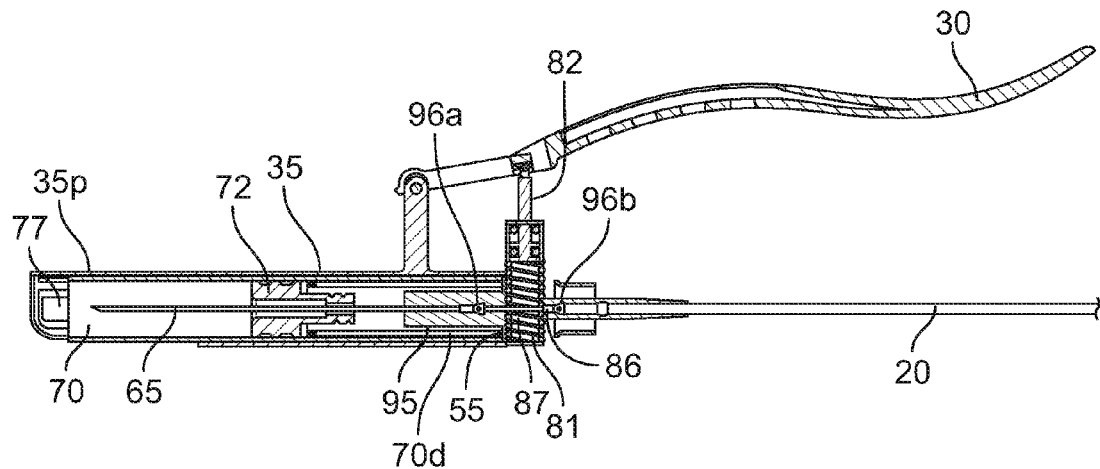
FIGS. 6A-B depict another vial embodiment featuring two check valves, in accordance with features of the present invention.

In still another embodiment, the housing 35 does not contain the piston 60, such that it is piston-less. Instead, fluid pressure generated during filling of the valve cavity 81 provides the means for drawing fluid from the vial 70. As in prior embodiments, the user loads the medicament vial 70 into the housing 35, wherein the needle 65 pierces the rubber vial stopper 72. A stationary ram 95, extending from the flat substrate 55, pushes against the stopper 72 during loading, causing the fluid in the vial 70 to fill the needle 65 and valve cavity 81. In this embodiment, the distal end 70d of the vial 70 contacts the flat substrate 55 when the vial 70 is fully loaded, and the tab 77 at the proximal end 35p of the housing 35 locks the vial 70 in place. Within the stationary ram 95 is a first check valve 96a. As depicted in FIG. 6A, the first check valve 96a is a ball valve. During loading, the first check valve 96a is open because of the fluid pressure on the ball, created as a result of the pressure exerted by the stationary ram 95 on the stopper 72. Because the first check valve 96a is open, fluid flows into the valve cavity 81. This expansion in volume from the needle 65 to the valve cavity 81 lowers the fluid pressure. Within the outlet 86 is a second check valve 96b. This valve is initially closed because the fluid pressure is not great enough to open the valve.

Figure 6B:
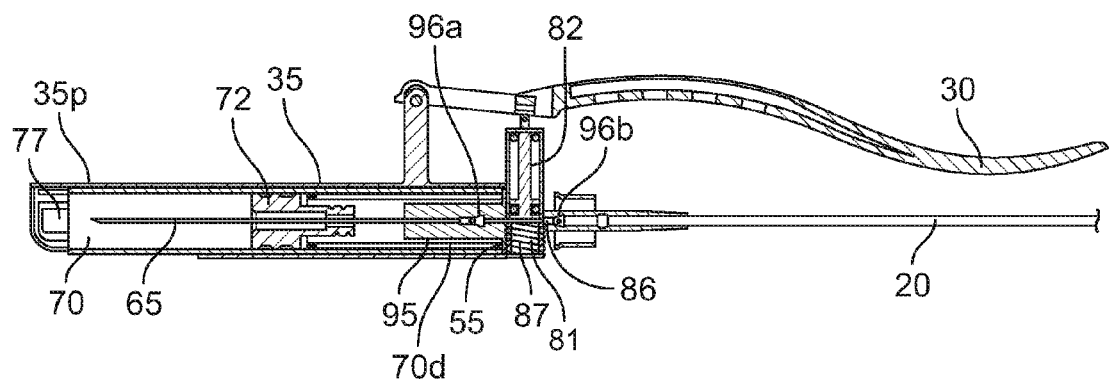

Upon depressing the actuation means 30 (FIG. 6B), the valve plunger 82 causes compression of the valve spring 87, increasing in pressure in the valve chamber as a result of the volume decrease. The increased pressure forces the first check valve 96a closed and opens the second check valve 96b. Thus, retrograde flow into the vial 70 is prevented and anterograde flow into the conduit 20 is allowed.

When the actuation means 30 is released, the compressed valve spring 87 forces the valve plunger 82 out of the valve cavity 81, creating a drop in pressure in the valve cavity 81. The decreased pressure or vacuum causes the second check valve 96*b* to close, while the also causing the first check valve 96*a* to open. The vacuum in the valve cavity 81 is then filled with fluid from the vial 70. The act of filling the vacuum also draws the stopper 72 further towards the proximal end 70*p* of the vial 70 so as to equalize the pressure. Each time the actuation means 30 is actuated the process repeats itself until the contents of the vial 70 are completely expelled.

Though the foregoing discussion primarily concerned a trigger as the actuation means, other actuation means are easily envisioned, especially for the pneumatically, hydraulically, and electrically actuated embodiments. The actuation means 30 could be a foot pedal that controls the linear motor, air compressor, or hydraulic pump that is in mechanical communication with the valve 80. Other suitable actuation means 30 include a button, toggle switch, pressure sensor, or voice command. Moreover, these actuation means can be contained on the device 10 or apart from the device, such as in the case of the foot pedal.

Syringe Embodiment

In a second embodiment of the present invention depicted in FIGS. 7A-7D, the dispenser 15 works in combination with a syringe 102. In some configurations of the second embodiment, a reservoir 100 is utilized to pressurize the fluid in the syringe 102. In other configurations, the syringe 102 is pressurized, either internally or externally, and connected directly to a pressure release valve 104 (as shown in FIG. 8A).

In configurations using a reservoir 100, the reservoir 100 is adapted to receive the syringe of anesthetic as depicted in FIG. 7A such that the reservoir is positioned between the syringe and the stylet 20. The reservoir defines a cavity which is isolated from the ambient environment. The syringe 102 is a typical one in that it comprises a barrel 105, a plunger 110 slidably received by one end of the barrel, and a tip 115 positioned at a second end of the barrel. Some syringe embodiments also feature finger tabs 117, which provide a means to apply pressure on the barrel 105 that opposes the pressure applied to the plunger 110. The tip 115 of the syringe 102 is in fluid communication with the reservoir 100. In a preferred embodiment, the tip 115 and the reservoir 100 connect via a luer taper or a luer lock. In a more preferred embodiment, the syringe 102 has a sealed tip and the mating surface of the reservoir has a means for puncturing the sealed tip when the tip is inserted into the reservoir's entry port. In this embodiment, the sealed tip and the mating surface have cross sections that are substantially identical so as to confer hermetic sealing between the two structures.

Luer tapers and luer locks create fluid tight seals between fluid carrying lines or needles. A luer taper connection consists of a male connector and a female connector. Both are frustoconical fittings wherein the female connector is adapted to receive the male connector. The standard taper for medical devices is about 6 percent. Some luer tapers feature a gasket inside of the female connector or outside the male connector to provide additional security against slippage. A luer lock similarly consists of tapered male and female connectors. However, the male connector also features a threaded housing around its periphery. The female connector features a flange about the top of its taper. Thus, as the male connector is received in the female connector, the flange on the female connector engages the threaded housing around the male connector to provide additional frictional engagement.

Upon affixing the syringe 102 to the reservoir 100, the contents of the syringe 102 are injected into the reservoir 100 by depressing the plunger 110 as can be seen in FIG. 7C. As more clearly depicted in FIG. 8A, the reservoir 100 has an entry port 120 with a one way valve 121 (depicted herein as a ball valve) that allows the contents of the syringe to enter the reservoir but blocks the contents of the reservoir from backing up into the syringe from where it came. In a preferred embodiment, the one way valve 121 is a ball valve. Some commercially available luer lock adapters incorporate a one way valve. These adapters are readily available in the medical field and are commonly placed in line (i.e., coaxially) between a standard syringe and intravenous port to prevent injected fluid from backing into the syringe. In another preferred embodiment, these adapters are used instead of incorporating a one-way valve into the reservoir.

The ball valve 121 consists of a channel 122 defining a longitudinal axis along which a ball 124 traverses. A spring 126 applies a force on the ball 124 in the direction of the entry port 120. (In this embodiment, the spring applies an axial force, relative to the channel.) A proximal end of the channel 122 defines a frusto-conical surface adapted to matingly receive the ball so as to prevent backflow into the entry port 120. The spring 126 is supported on a base 130, which itself is formed from a depending end of the channel such that the base is positioned between fluid ingress apertures. When the anesthesiologist depresses the plunger 110, the fluid pressure forces the ball 124 to compress the spring 126. In doing so, the entry port 120 is no longer blocked and fluid can flow through the channel 122 into the reservoir 100. When the anesthesiologist removes the pressure on the plunger 110, the spring 126 and elevated pressure in the reservoir push the ball 124 back into the entry port 120, sealing it. In some embodiments, the spring 126 is omitted and only the elevated pressure in the reservoir pushes the ball to block fluid flow. The fluid that remains in the reservoir 100 is pressurized for dispersion.

Figure 8A:
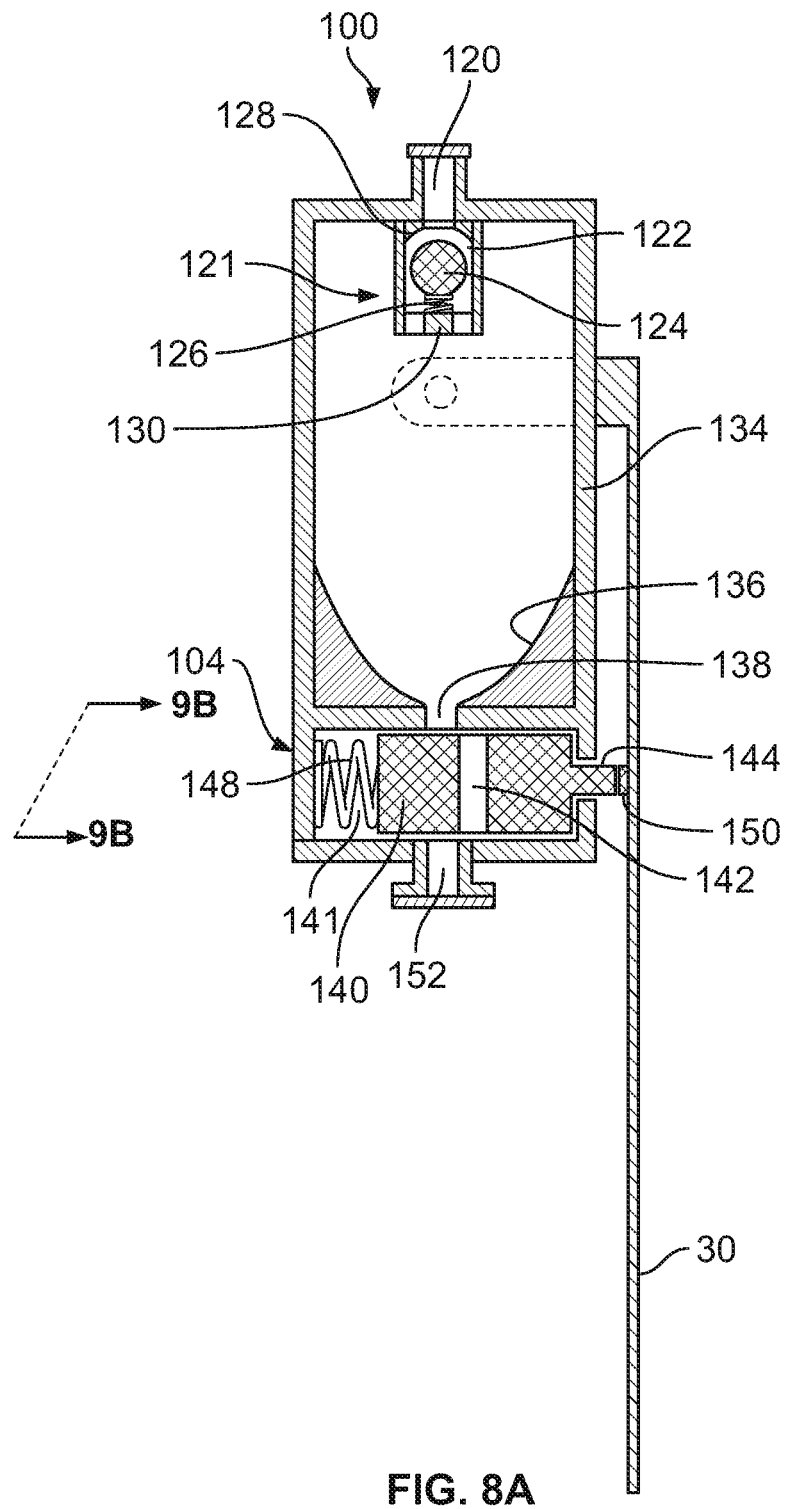
FIG. 8A is a sectional view of FIG. 7E taken along line 8A-8A.

The fluid is held in the reservoir 100, pending dispersion, via a pressure relief valve 104. The reservoir 100 is a chamber with perimeter walls 134 and a chamber floor 136. An outlet 138 is formed into the chamber floor 136. In some embodiments, as depicted in FIG. 8A, the chamber floor 136 is angled so as to funnel the contents of the reservoir towards the outlet 138. The pressure relief valve 104 blocks flow through the outlet 138 until the valve is actuated via the actuation means 30.

As can be seen in FIGS. 7B-7C, the pressure relief valve 104 features a movable block 140 inside of the valve chamber 141. The block defines a periphery of two different surfaces. A first surface has a cross section similar in shape to interior of the chamber but slightly smaller so as to allow radial and medial movement of the block in the valve chamber such that the movement is generally perpendicular to the longitudinal axis of the chamber. This first surface circumscribes approximately two-thirds of the block. A second surface defines a chord which intersects the first surface. Midway along the chord, and proximal to the chord edge, a region of the block defines a through-hole, such as transverse aperture 142. Approximately on the other side of the block and midway along the first surface exists a radially extending protrusion 144. The protrusion 144 is matingly received by a port 146 formed in the side of the reservoir 100, such that a portion of the protrusion 144 is outside of the reservoir 100.

When the pressure relief valve 104 is at rest, a spring 148 biases the movable block 140 radially so as to contact one side of the valve chamber 141. In the rest position, the through-hole 142 and the outlet 134 do not align or overlap at all; thus, no flow from the reservoir 100 occurs. When the anesthesiologist actuates the actuation means 30, a nub 150 on the actuation means 30 contacts the protrusion 144 and urges it in a medial direction. In doing so, the user inputted force on the actuation means 130 is transferred through the nub 150 to the movable block 140. This action compresses the spring 148, forcing the block to move radially toward the center of the chamber allowing the through-hole 142 to align with the egress outlet 138. When the through-hole 142 and outlet 134 are brought into alignment, the pressurized fluid flows through the pressure relief valve 104 and out of the reservoir through an opening 152. The opening 152 is in fluid communication with the malleable conduit 20.

Though a pressure relief valve is discussed as a portion of the primary embodiment. Other valves are also suitable. In some embodiments, especially those with electrical actuation means, the valve could be a solenoid valve. Solenoid valves are typically closed until electrically activated; thus, activation of the electrical actuation means also activates the solenoid valve. This solenoid valve can be actuated electrically via current flow or wireless communication, such as infrared or radio frequency communication. Another possible valve is a clamping valve. This valve could be activated electrically via current flow or wireless communication, such as through radio-frequency and infrared signals, or mechanically via pneumatic or hydraulic actuation. The clamping valve would be biased in the closed position to restrict flow through a soft and deformable channel between the reservoir or syringe and the conduit. Still another potential valve is a multi-position valve. The multi-position valve remains closed until an open channel is selected by rotating to or unblocking the flow path. This valve would be particularly useful with the embodiments of the invention in which continuous pressure is applied to the plunger 110. This listing of valve types is meant to be illustrative and not limiting; other valves could also be used as part of the present invention.

As depicted in FIGS. 7B-7D, a syringe 102 is attached to the reservoir 100. The plunger 110 is depressed, forcing the contents into the reservoir 100 where the contents become pressurized. Because the one way valve blocks backflow, the syringe 102 can then be removed. Preferably the syringed is removed prior to intubation of the patient because the syringe can interfere with the anesthesiologist's vision during the intubation procedure. Also, the syringe adds additional weight to the top of the ETT, creating a top heavy device that may hit the patient in the face during an intubation procedure.

Figure 7E:
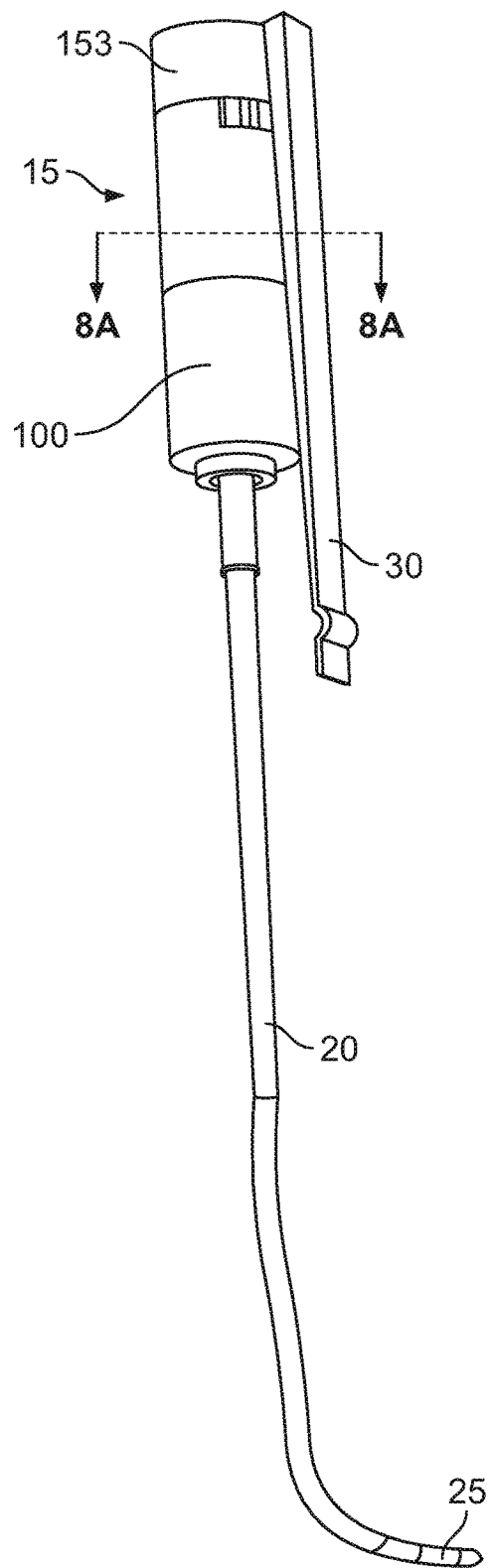
FIG. 7E depicts a gas pressurized syringe embodiment, in accordance with features of the present invention.

When the pressure relief valve is opened the fluid will flow out the nozzle based on the pressure gradient that exists between the pressurized container 100 and the nozzle 25 which is at ambient pressure. The one way 121 prevents fluid movement in the opposite direction out of the container 100 or back into the syringe if it is still connected. This valve 121 remains closed during this process because of the pressure differential that also exists between the chamber 100 under pressure and the ambient pressure or the pressure in the syringe. Alternatively, as shown in FIG. 7E, a pressurized vessel 153 of carbon dioxide or air can be affixed to the reservoir 100 after removing the syringe 102. The pressurized fluid will ensure that the contents of the reservoir 100 remain pressurized throughout the course of intubation. In still another alternate design, the syringe or vial and pressurized gas vessel are sold as a single pre-configured cartridge for pressurized deliver of anesthetic via an LTA device. Such cartridges are commercially available, such as the J-Tip® Needle-Free Injection System, available from National Medical Products, Inc. (Irvine, Calif.).

Figure 9A:
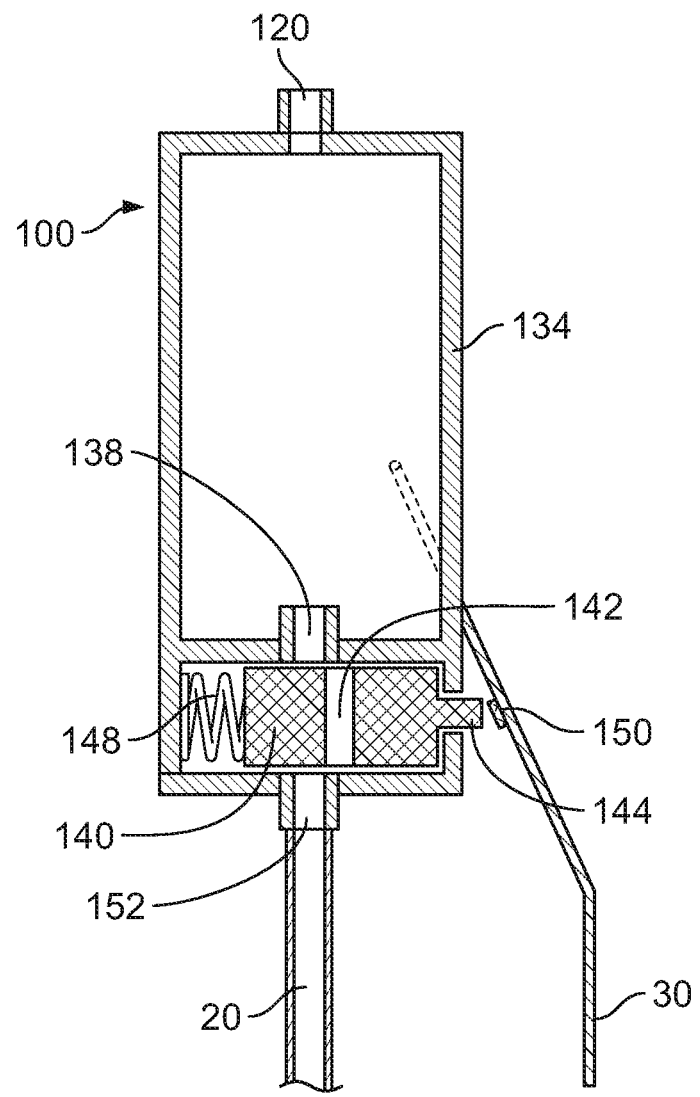
FIG. 9A depicts an embodiment of the reservoir without a one-way valve, in accordance with features of the present invention.
Figure 9B:
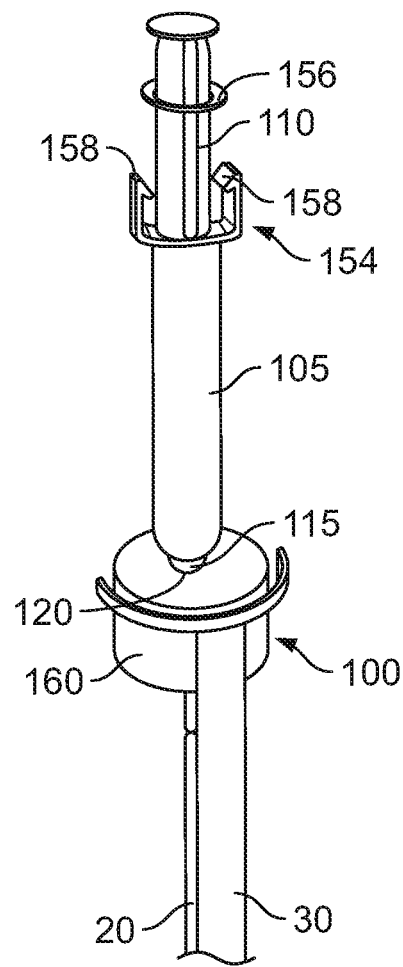
FIGS. 9B-C depict a locking syringe embodiment of the device, in accordance with features of the present invention.
Figure 9C:
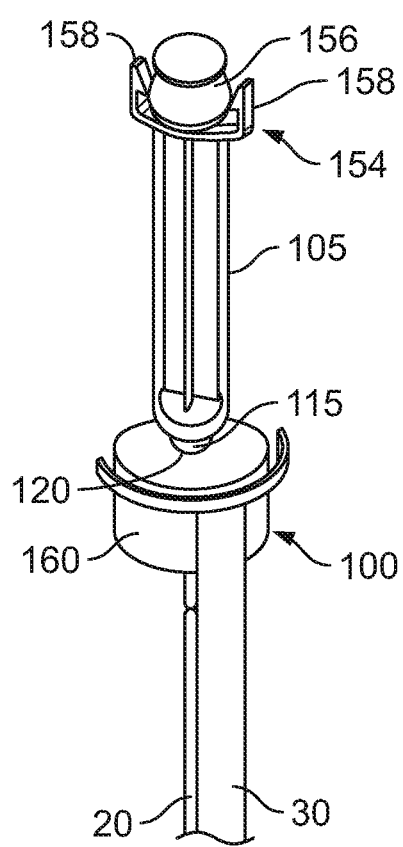

In another configuration depicted in FIG. 9A, the reservoir 100 does not use a one-way valve 121. Instead, the syringe 102 or housing 160 features a locking mechanism 154, which can be seen in FIG. 9B-9C. The anesthesiologist connects the syringe 102 to the entry port 120. After establishing fluid communication between the syringe 102 and the reservoir 100, the anesthesiologist depresses the plunger 110. A stop 156 on the plunger 110 engages the locking mechanism 154 that is mounted to the proximal end 105$p$ of the barrel 105. As depicted in FIGS. 9B-9C, the locking mechanism 154 is two clips that extend vertically from the barrel 105. As the plunger 110 is depressed, the stop 156 deflects tapered flaps 158 on the clips from away from the plunger 110 path. Once the stop 156 passes the tapered flaps 158, the clips recover to their original position and lock the syringe 102 in place.

Locking the syringe prevents fluid pressure from pushing the plunger 110 back towards the drawn position. Because the plunger 110 exerts positive pressure on the contents of the syringe and contents of the reservoir 100, the fluid cannot undergo retrograde flow, and the contents are pressurized for delivery. Delivery in this embodiment is similar to the previous embodiment in which the pressure relief valve 104 is activated by the actuation means 30.

In still another configuration of the syringe embodiment, syringe 102 is connected directly to the pressure relief valve 104. In this configuration, the contents of the syringe 102 are not pressurized in the reservoir. Instead, the pressure is provided from within the syringe 102 or from an external force. In prior art devices, the anesthesiologist was forced to apply pressure to the syringe, but in doing so, the anesthesiologist could not maintain his hands in the proper intubation position.

Figure 10A:
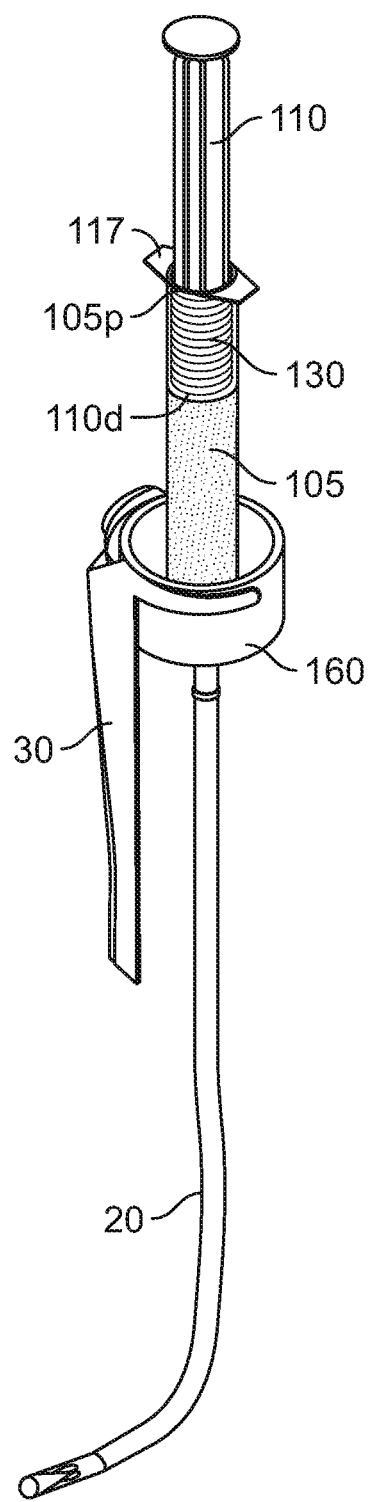
FIGS. 10A-B depict an embodiment with a syringe featuring an internal spring, in accordance with features of the present invention.
Figure 10B:
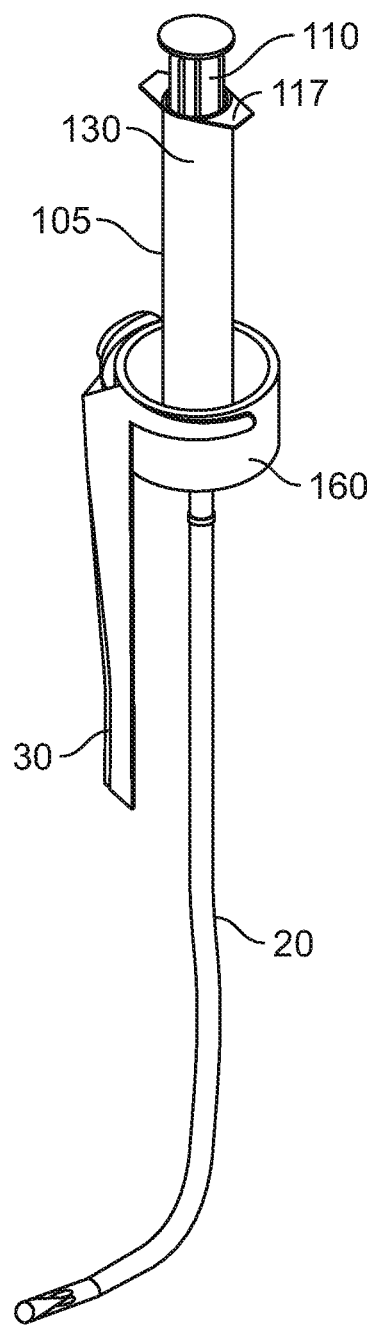

In one configuration depicted in FIG. 10A, a specialized syringe 102 is utilized. In this embodiment, the barrel 105 of the syringe houses a spring 130. One end of the spring 130 is attached to the proximal end of the barrel 105$p$, while the second end of the spring 130 is attached to the distal end of the plunger 110$d$. As shown in FIG. 10A, the spring 130 is compressed as the distal end of the plunger 110$d$ is spatially disposed of the distal end of the barrel 105$d$. When the syringe is filled with anesthetic, or another medicament, the fluid pressure keeps the plunger 110$d$ in the drawn position. As the fluid flows out of the syringe 102, the fluid level in the syringe 102 lessens, which allows the spring 130 to depress the plunger 110. FIG. 10B depicts the plunger fully depressed with the spring substantially relaxed. Thus, the compression in the spring 130 causes the plunger 110 to keep continuous pressure on the fluid in the syringe 102.

The syringe 102 is in fluid communication with the pressure relief valve via a luer lock, with or without a piercable membrane such as that described supra. If the syringe is prefilled with an anesthetic or a medicament, preferably the luer tip contains the piercable membrane. If, alternatively, the syringe 102 is filled by aspiration anesthetic or medication from a vial, then the user would have to hold back the plunger 110 until the syringe 102 is connected to the pressure relief valve 104. Spring-loaded syringes are commercially available, such as the Episure™ AutoDetect LOR Syringe, distributed by Indigo Orb, Incorporated (Santa Clara, Calif.).

Figure 8C:
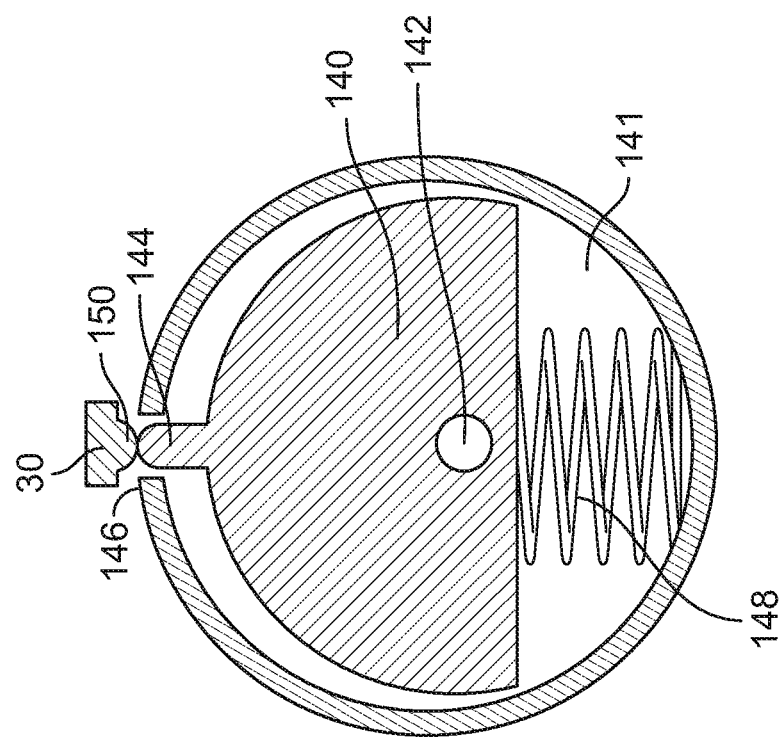
FIGS. 8B-C depict sectional views taken along line 8B-8B as shown in FIG. 8A.
Figure 8B:
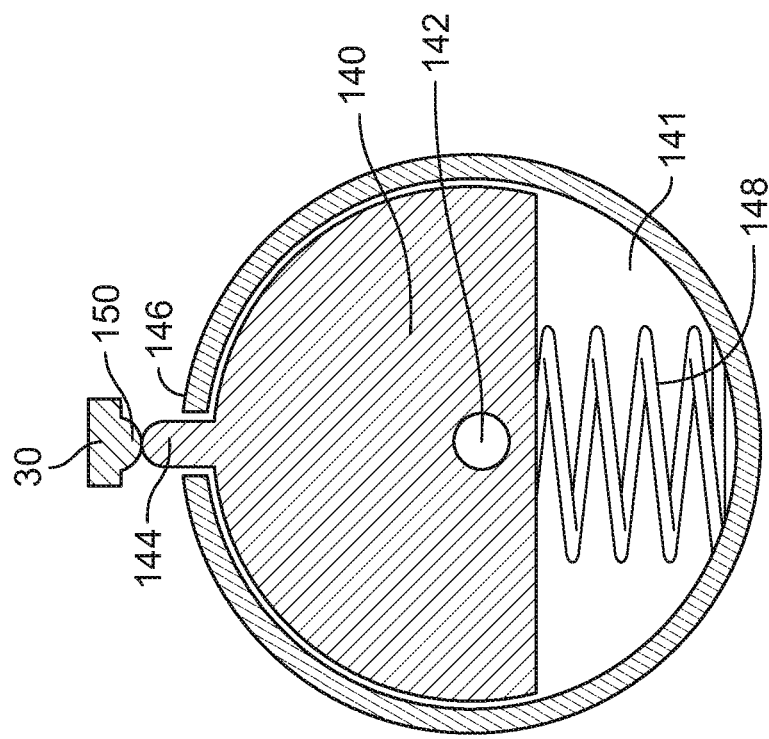

The syringe 102 is in fluid communication with the pressure relief valve 104. Preferably, fluid communication is established via a luer lock or luer taper; however, other sealed connections are also suitable. The pressure relief valve 104 operates in the same fashion as in the other configurations and embodiments. The actuation means 30 is rotatably mounted to a housing 160. The housing 160 can be the outer wall of the pressure relief valve 104, or the housing 160 can extend over the pressure relief valve 104. As depicted in FIGS. 8B-8C, the actuation means 30 is in mechanical communication with a movable block 140, which contains a through-hole 142. In this configuration, when the through-hole 142 aligns with the luer lock, luer taper, or other connecting means, the contents of the syringe 102 can flow into the conduit 20.

Figure 11:
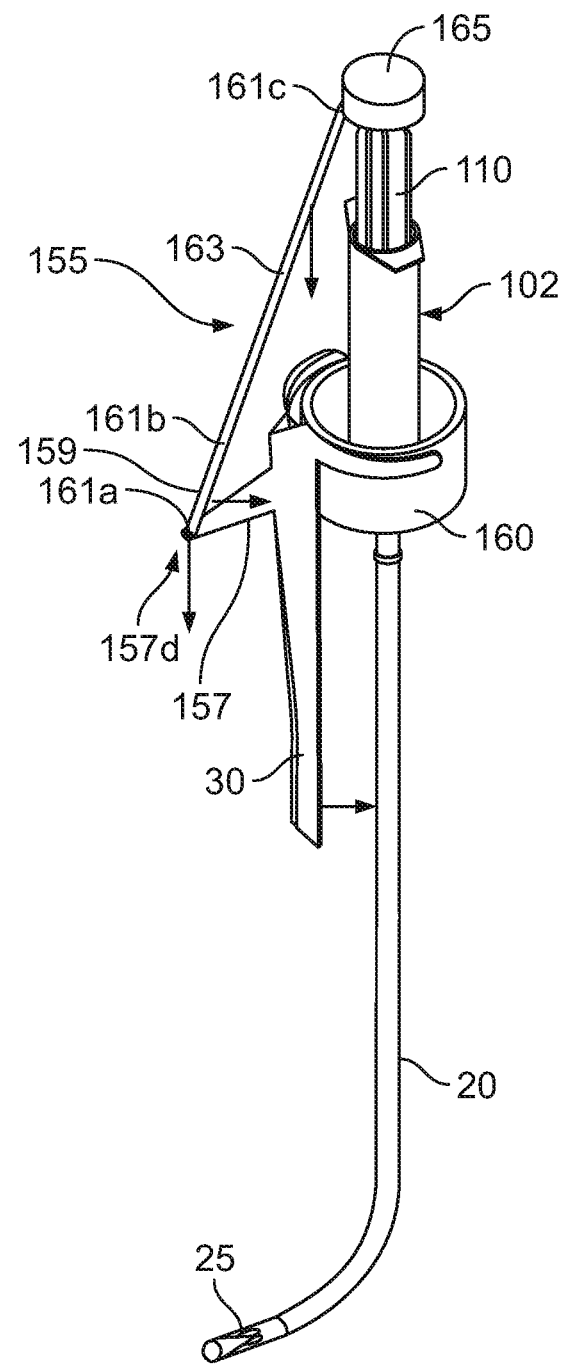
FIG. 11 depicts an embodiment of the LTA device featuring a linkage mechanism, in accordance with features of the present invention.

In another configuration, an ordinary syringe 102 is used and pressure is applied to the plunger 110 via a 4-bar linkage mechanism 155. As depicted in FIG. 11, a bar 157 extends from the actuation means 30. The distal end 157$d$ of the bar 157 is connected to a first link 159 via first pivot joint 161$a$. The first link 159 is, in turn, connected to a second link 163 via a second pivot joint 161$b$. The second link 163 is connected to a plunger cap 165 via a third pivot joint 161$c$. When the actuation means 30, or trigger, is pulled, the rotational movement of the trigger is transferred through the bar 157 to the linkage mechanism 155. The distal end 157$d$ of the bar 157 rotates downwardly as depicted by the arrows in FIG. 11. This pulls the first link 159 towards the device 10, which translates to a downward pull on the second link 163. The second link 163 pulls downwardly on the plunger cap 165, which forces the plunger 110 downward as well. Additionally, pulling on the trigger actuates the pressure relief valve 104, releasing the contents of the syringe into the conduit 20.

Figure 12A:
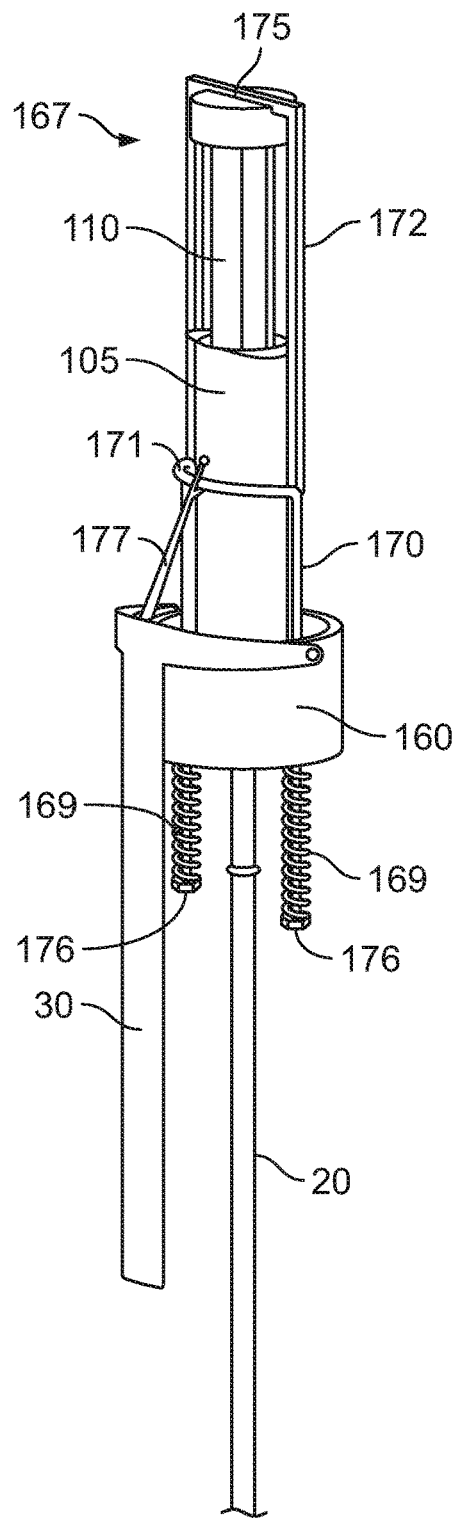
FIGS. 12A-D depict an embodiment of the LTA device featuring a sling mechanism, in accordance with features of the present invention.

In still another configuration as can be seen in FIG. 12A, a sling mechanism 167 is placed over the top of the plunger 110. The sling mechanism 167 is comprised of a plurality of springs 169 located on the bottom of the housing 160. Coaxial with the springs 169 are vertical extenders 170 that extend through the housing 160. A locking bar 171 is connected to the two vertical extenders 170. Vertical arms 172 extend from the vertical extender 170 and locking bar 171 combination. The vertical arms 172 are spanned at their uppermost end by a horizontal cap 175. The anesthesiologist pulls the cap 175 towards the top of the plunger 110. Blocks 176 on the end of the vertical extenders 170 causes the springs 169 to become compressed. The anesthesiologist then slips the cap 175 over the top of the plunger 110. The locking bar 171 moves with the cap 175, and in doing so, the locking bar 171 moves past a blocking pin 177 that is connected to the actuation means 30. Once the cap 175 is positioned atop the plunger 110, the locking bar 171 engages the blocking pin 177, which prevents the plunger 110 from depressing.

When the actuation means 30 is pulled inwardly, the blocking bar 177 is pulled outwardly via rotational movement. Doing so removes the blocking pin 177 from the path of the locking bar 171, and the springs 169 attempt to recover to their original expanded position. The expansion of the springs 169 pulls on the vertical extenders 173 via the blocks 176, which, in turn, pull on the vertical arms 172 and cap 175. Thus, the sling mechanism provides continuous pressure on the plunger 110. As shown in FIG. 12A, the blocking pin 177 has already been removed and the cap 175 is applying a downward pressure on the plunger 110. Like the other configurations, interaction with the actuation means 30 opens the pressure relief valve 104 so that the contents of the syringe 102 can flow into the conduit 20.

Figure 12B:
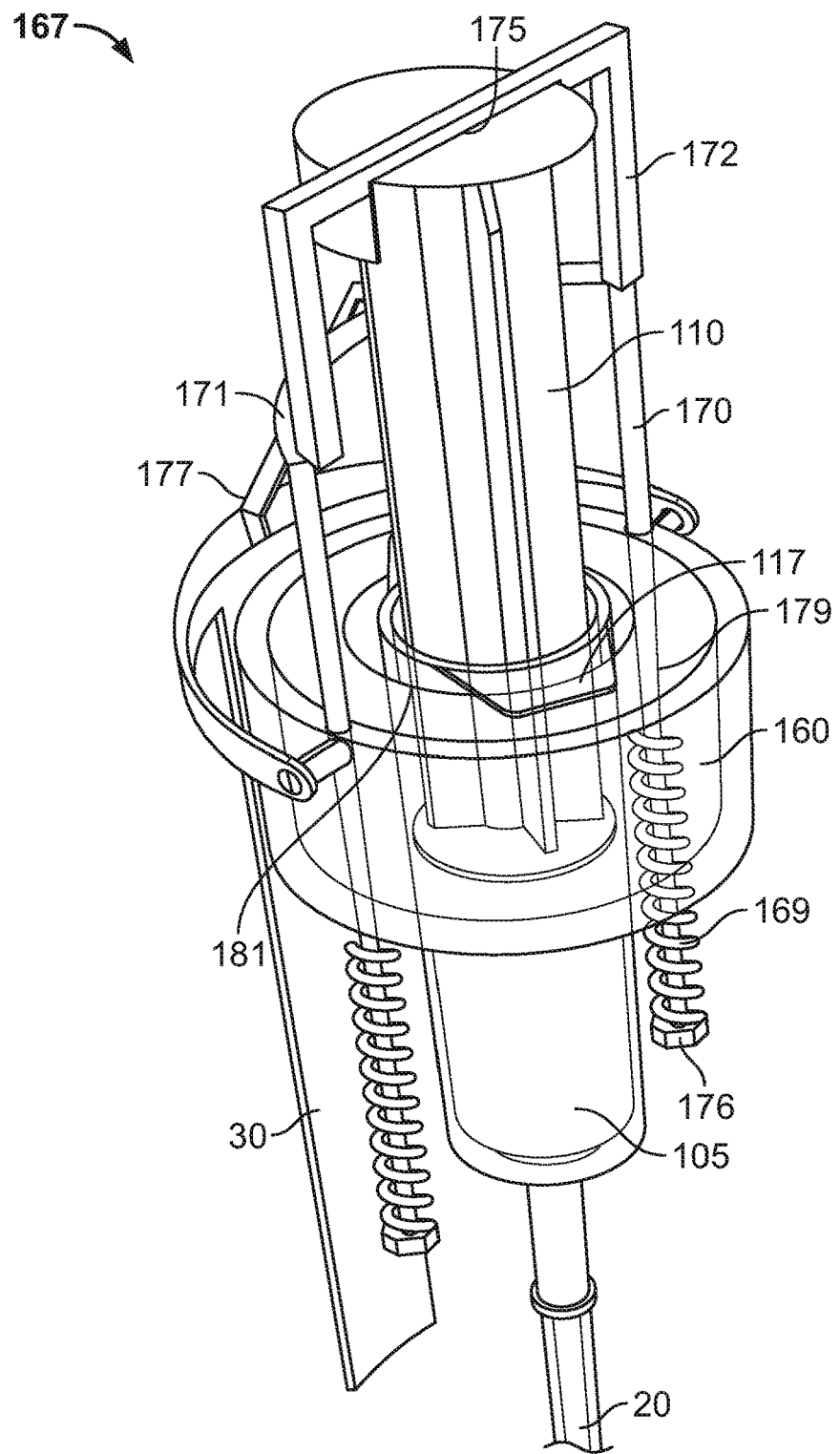

FIG. 12B shows an alternate design of this configuration in which the tip 115 of the syringe 102 is connected directly to the conduit 20 via a luer lock, luer taper, or other similar connection means. The actuation means 30 is mounted on the housing 160. The housing 160 features a top substrate 179 with a central opening 181. The central opening 181 allows passage of the syringe barrel 105 but not the passage of the finger tabs 117. Like the previous design, the sling mechanism 167 is extended over the top of the plunger 110 and provides downward pressure on the plunger 110. This design does not feature a pressure relief valve. Instead, the fluid is held inside the syringe because the relatively small amount of pressure pushing down on the liquid, while the blocking pin is in place, is overcome by the atmospheric pressure in the conduit 20 pushing up. Additionally, the surface tension of the fluid prevents drops from forming and dripping through the conduit 20. One advantage of the design depicted in FIG. 12B is that the dispensing mechanism is reusable because none of the contents of the vial come in contact with the dispenser. The conduit 20 and syringe 102 would be replaced in future uses.

Figure 12C:
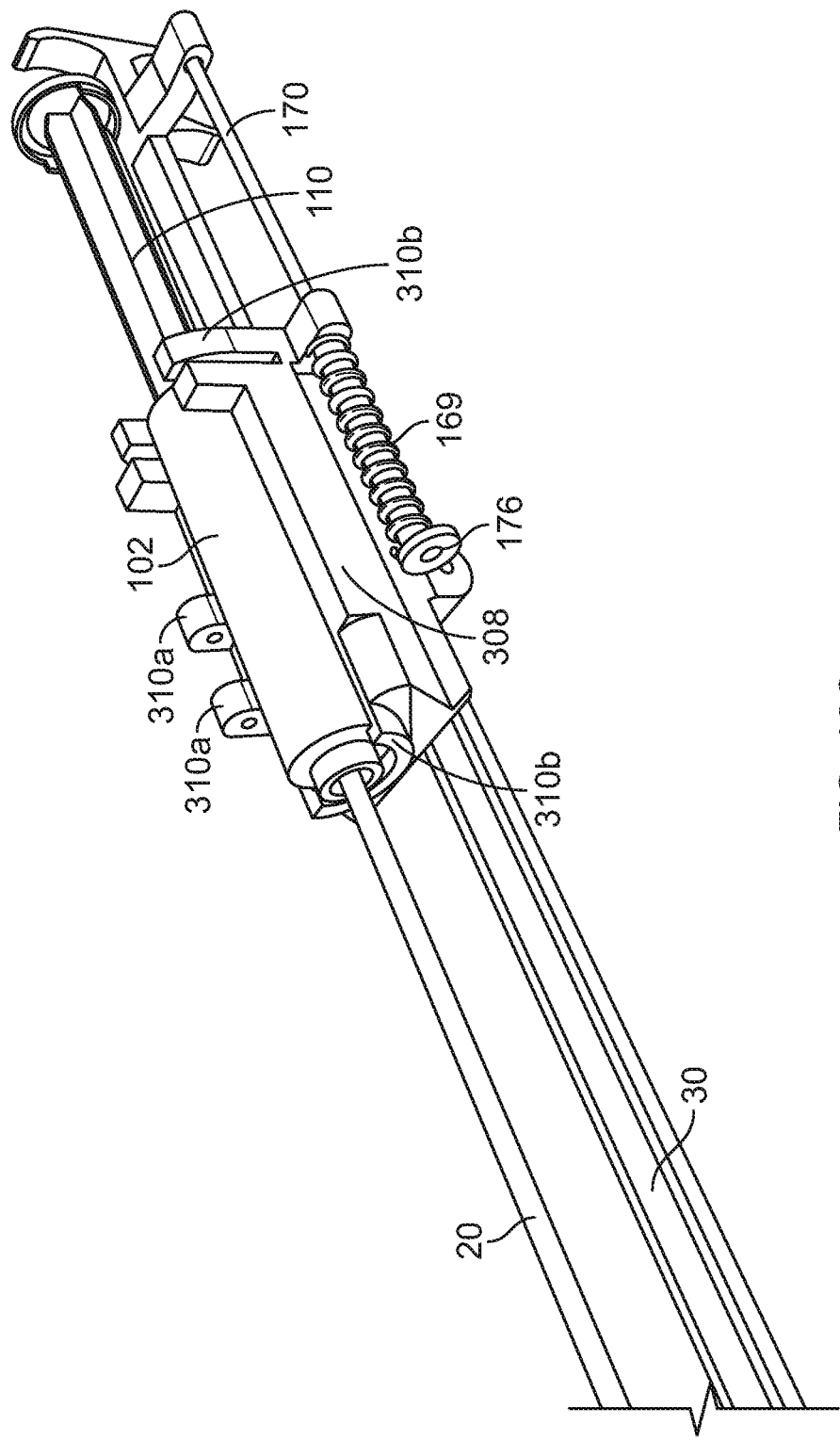
Figure 12D:
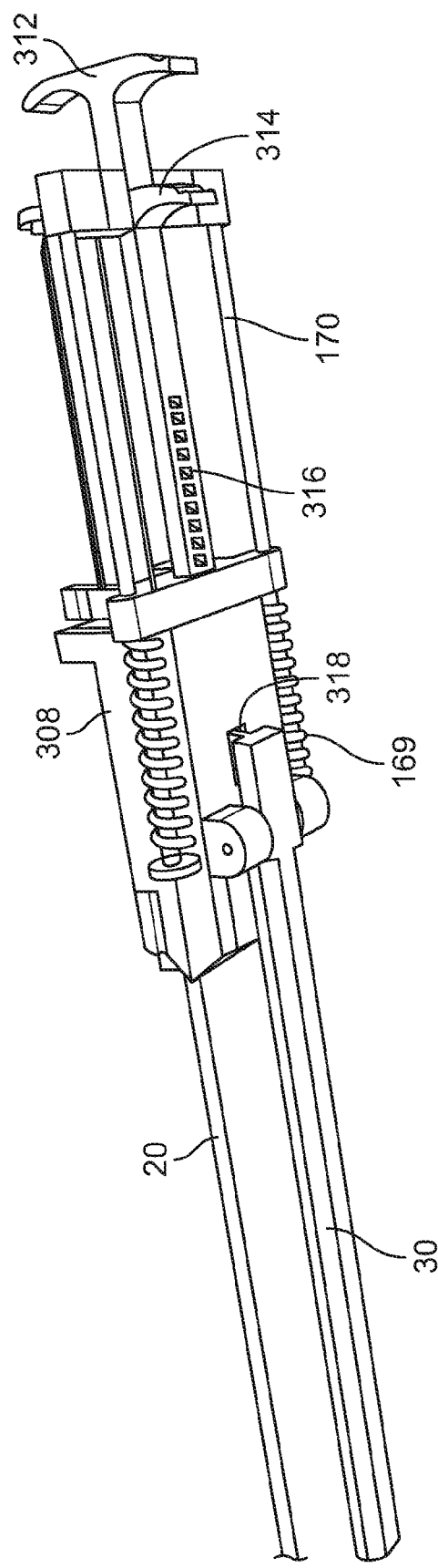

FIGS. 12C-D shows another alternate design of the sling mechanism 167. The syringe 102 is placed in a cradle 308. The syringe is held firmly in place with a plurality of securing members 310. These latitudinal securing members 310a have a gripping surface made of rubber or a similar material such that they frictionally engage the syringe 102 when it is snapped into the cradle 308. Longitudinal securing members 310b lock the prevent the syringe from slipping out downwardly when the LTA device 10 is held upright and prevent the syringe from pulling out of the cradle 308 when the plunger 110 is drawn. Like the previous embodiments, the cradle 308 features vertical extenders 170 with springs 169 extending between the cradle 308 and the blocks 176 on the depending end of the vertical extenders 170. At the top of the vertical extenders 170 is a cap 175. In this embodiment, the cap optionally features a handle 312 to aid in pulling the sling mechanism 167 over the plunger 110. The cap 175 does not directly exert pressure on the plunger 175; instead, projections 314 engage the top of the plunger 110 to provide downward force.

Another feature of the embodiment shown in FIGS. 12C-D is the pin and slot locking mechanism. Extending downwardly from the cap 175 and through the cradle 308 is a slotted bar 316. The actuation means 30 features a pin (not shown) that engages the slot through a cavity 318 in the cradle 308. When the pin engages a slot on the slotted bar 316, the slotted bar 316 is prevented from moving. Because the slotted bar 316 is in mechanical communication with the cap 175, the sling mechanism 167 is also prevented from moving. Thus, when the actuation means 30 is actuated, the pin is removed from the slotted bar 316 and the sling mechanism 167 and plunger 110 will begin to lower. When the user releases pressure on the actuation means 30, the pin will slide into another slot on the slotted bar 316, stopping movement of the bar and consequently pressure on the plunger 110.

Figure 13:
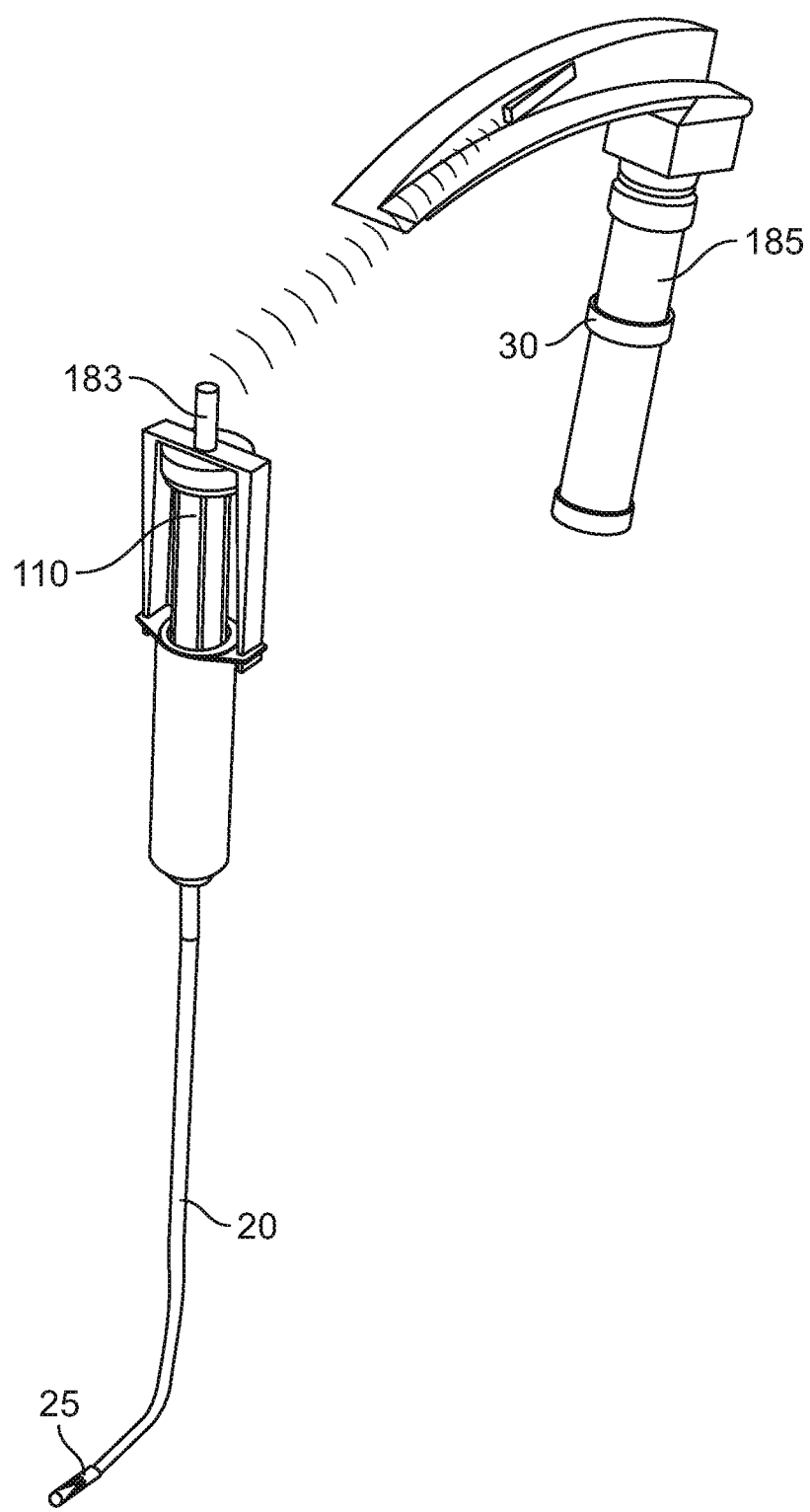
FIG. 13 depicts an embodiment of the LTA device featuring a co-axial electric motor controlled by an actuation means on a direct laryngoscopy blade.

In still another configuration, pressure is applied to the plunger via a separate electromechanical device. For instance, as shown in FIG. 13, the plunger 110 is driven by a linear electric motor 183, such as a linear magnetic motor or a piezoelectric motor. Additionally, the motor can be a rotational motor linked to a gear mechanism, such as a worm gear, to provide linear movement. Advantageously, these motors can be controlled using a variety of actuation means 30. Buttons, foot pedals, switches, and pressure plates are all forms of actuation means that can be in electrical or wireless communication with the pressure release valve 104, or any of the other potential valve types. In one configuration, depicted in FIG. 13, the actuation is carried out via wireless infrared communication, wherein the communicator is located on a direct laryngoscopy blade handle 185.

The foregoing discussion of dispensing mechanisms, actuation means, and valve controls is not meant to be limiting. Many of the dispensing mechanisms, actuation means, and valve controls can be combined with other mentioned or unmentioned dispensing mechanism, actuation means, and valve control combinations not presented here.

Conduit and Nozzle Detail

The conduit 20 provides fluid communication between the dispenser portion 15 of the device 10 and the nozzle 25. During an intubation procedure, the conduit 20 is substantially enclosed in an ETT 31. The ETT 31 is typically made from a flexible polymer tube, such as PVC, high- or low-density polyethylene, and polypropylene, among others. The ETT 31 is first slid over the conduit 20 and the conduit 20 and ETT 31 combination is then formed to the desired shape. The dispenser portion 15 engages the first end of the ETT 31 via a reversible frictional engagement, such as a standard straight slip joint connector found on most endotracheal tube connectors.

The LTA device 10 should be easily removable after the intubation procedure is complete so that general anesthesia and patient ventilation can begin being administered. During a typical intubation it can be difficult many times to remove the stylet from the endotracheal tube as a result of the static friction holding the LTA device in the ETT. Because the anesthesiologist's hands are occupied with the ETT and the laryngoscope, many times an assistant is required to disengage the stylet from the ETT while the anesthesiologist holds the ETT in place in the trachea or slides the ETT further into the trachea. Some anesthesiologists have become adept at moving their hand up the ETT and then using their thumb to dislodge the stylet. This technique, however, requires a high level of skill and dexterity, and the ETT can easily become displaced.

Figure 14A:
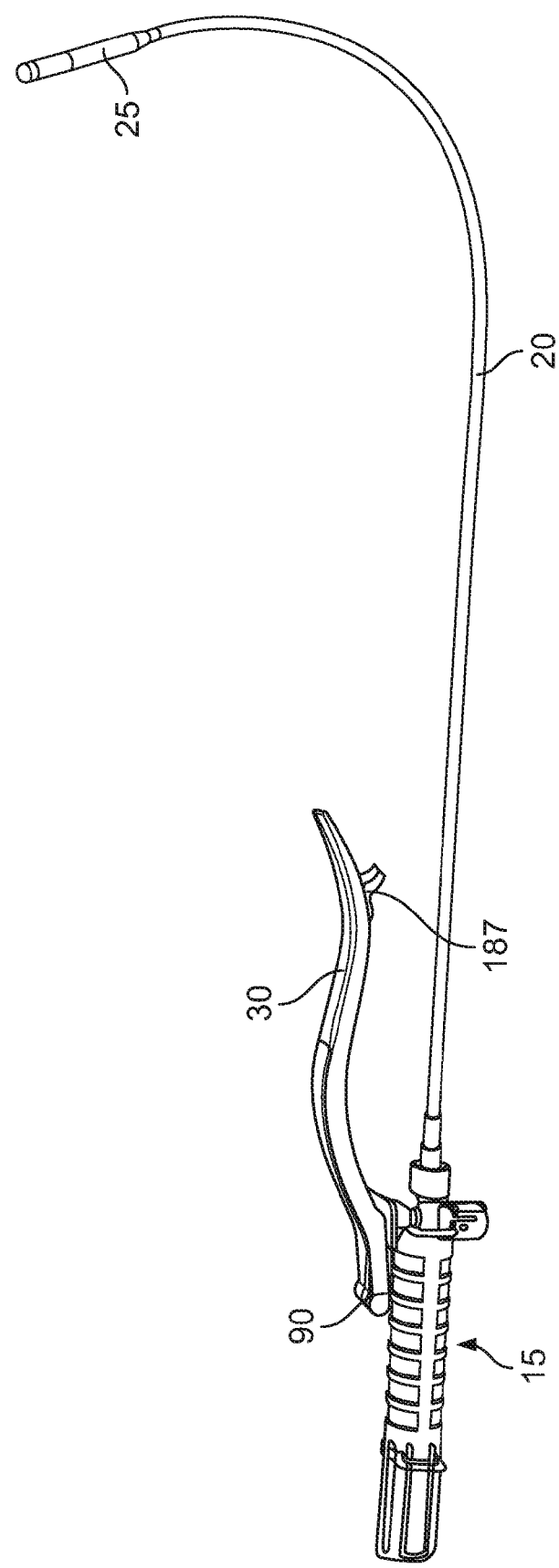
FIGS. 14A-B depict a tab on the actuation means that facilitates removal of the stylet from the ETT, in accordance with features of the present invention.
Figure 14B:
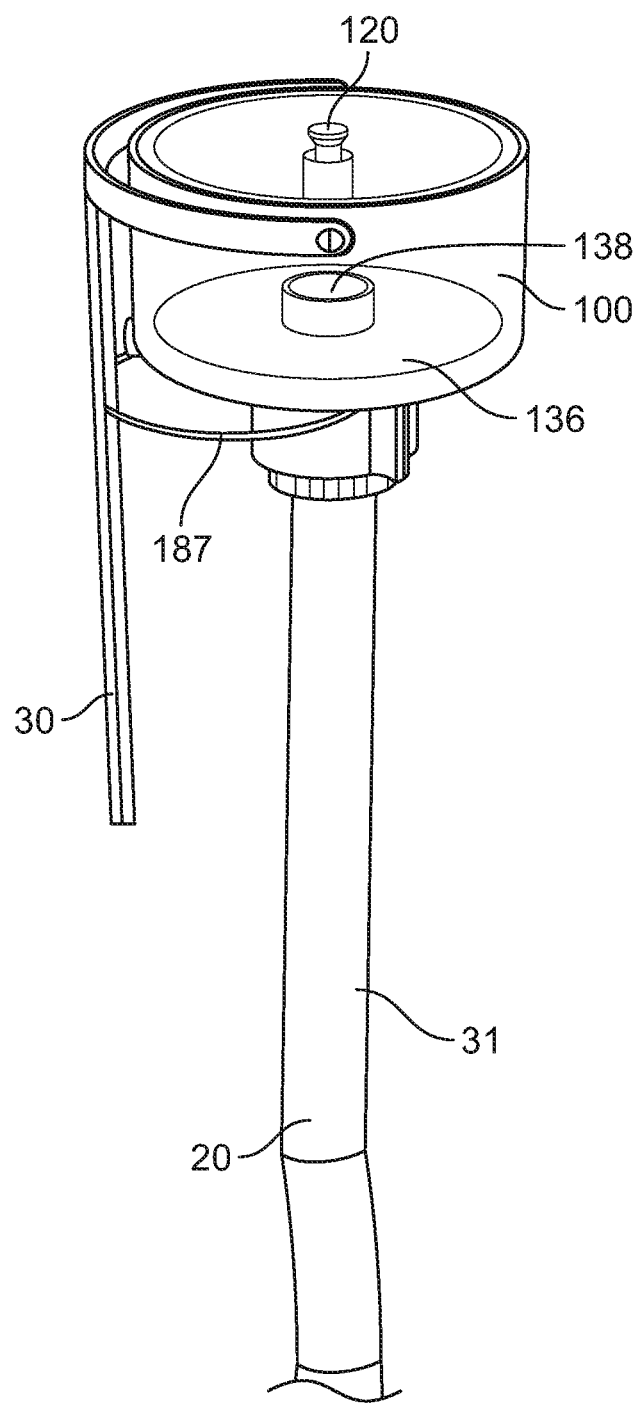

As shown in FIG. 14A, the present invention features a tab 187 projecting from the actuation means 30. The tab 187 allows a user to push his thumb or fingers against the tab 187, gaining leverage, and forcibly displace the LTA device 10 at least partially out of the ETT. In some designs, the surface of the tab 187 is fluted to facilitate frictional engagement between the tab and finger. The tab 187 may also be concave so as to better receive the distal or intermediate phalanges of a finger. Further, in these embodiments, the actuation means 30 may be prevented from rotating about the fulcrum 90 in a fashion opposite to the direction of actuation. This helps ensure that pressure applied by the finger results in upward displacement, and not reverse rotation of the actuation means. Alternatively, as shown in FIG. 14B, the tab 187 can directly engage and apply a force to the proximal end 31p of the ETT 31, resulting in forward displacement of the ETT 31 over the conduit 20 as the lever is depressed. The tab 187 is linked to the actuation means 30 such that of depressing the trigger causes the tab 187 to engage the ETT 31, which displaces the ETT 31.

A salient feature of the LTA device 10 is the ability to function as a combined stylet and introducer during an intubation procedure. To that end, the conduit 20 is made from a malleable material such that the conduit 20 can be reversibly deformed into a variety of shapes. The inventor has found 13-gauge 304 stainless steel hypodermic tubing to be a suitable material. This material has an outside diameter of 0.0950", an inside diameter of 0.071", and a wall thickness of 0.012". A variety of other non-toxic, biocompatible materials that are hollow and deformable would also work. Additionally, the stylet could be pre-formed or molded to the desired shape and serve as the conduit 20 for the LTA device 10.

Two commonly used intubation-aiding shapes are acuate and straight-to-cuff. The arcuate shape provides a semi-rigid guide that is in the natural shape of the ETT. The straight-to-cuff shape, as the name implies, provides a stylet that keeps the length of the ETT straight until the balloon cuff is reached. The stylet is then bent at approximately between a 35.degree. and 80.degree. angle, which causes the ETT to resemble a hockey stick. Larger or greater angles can be used depending on user preference and on the circumstances of the intubation. The straight-to-cuff shape can provide better visualization of the glottis in some circumstances.

The proximal end 31p ETT 31 is slid over the nozzle 25 and conduit 20 until it reaches the dispensing portion 15. The dispensing portion 15 and the proximal end 31p of the ETT 31 frictionally engage and the combined device is ready for intubation. Then, the LTA device 10 and ETT 31 combination is formed to the arcuate, straight-to-cuff, or other desired shape. The anesthesiologist performs a direct laryngoscopy of on the patient and the LTA device 10 and ETT 31 are introduced through the patient's mouth. As needed, the anesthesiologist dispenses local anesthetic to portions of the airway such as the tracheobronchial tree, along vocal cords, and portions of hypo-pharynx, including the epiglottis. Any of the previously discussed dispensing means can transfer the anesthetic from the cartridge to the conduit 20. The conduit 20 provides the fluid passageway to the nozzle 25, which expels the anesthetic in the form of a spray.

Figure 15A:
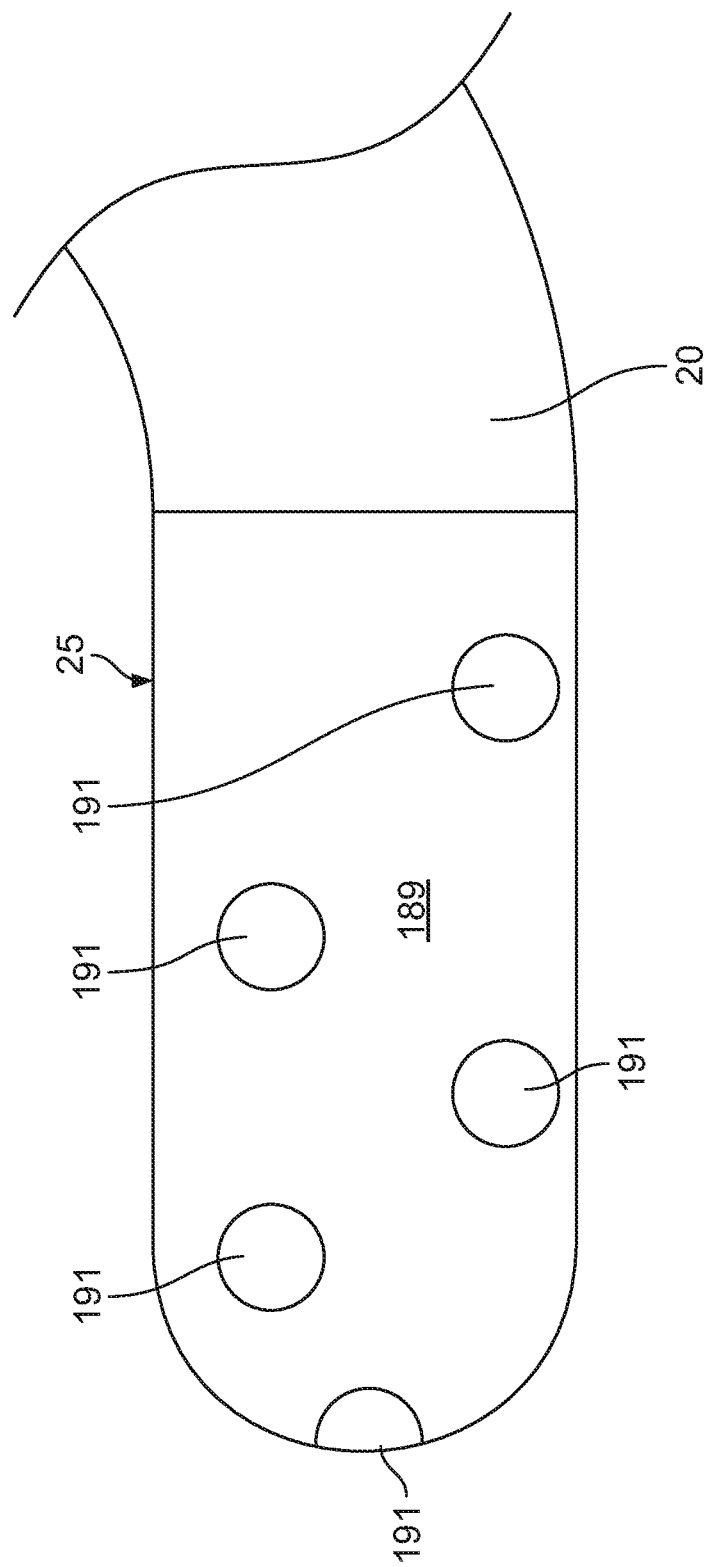
FIGS. 15A-B depict embodiments of the nozzle of the device, in accordance with features of the present invention.
Figure 15B:
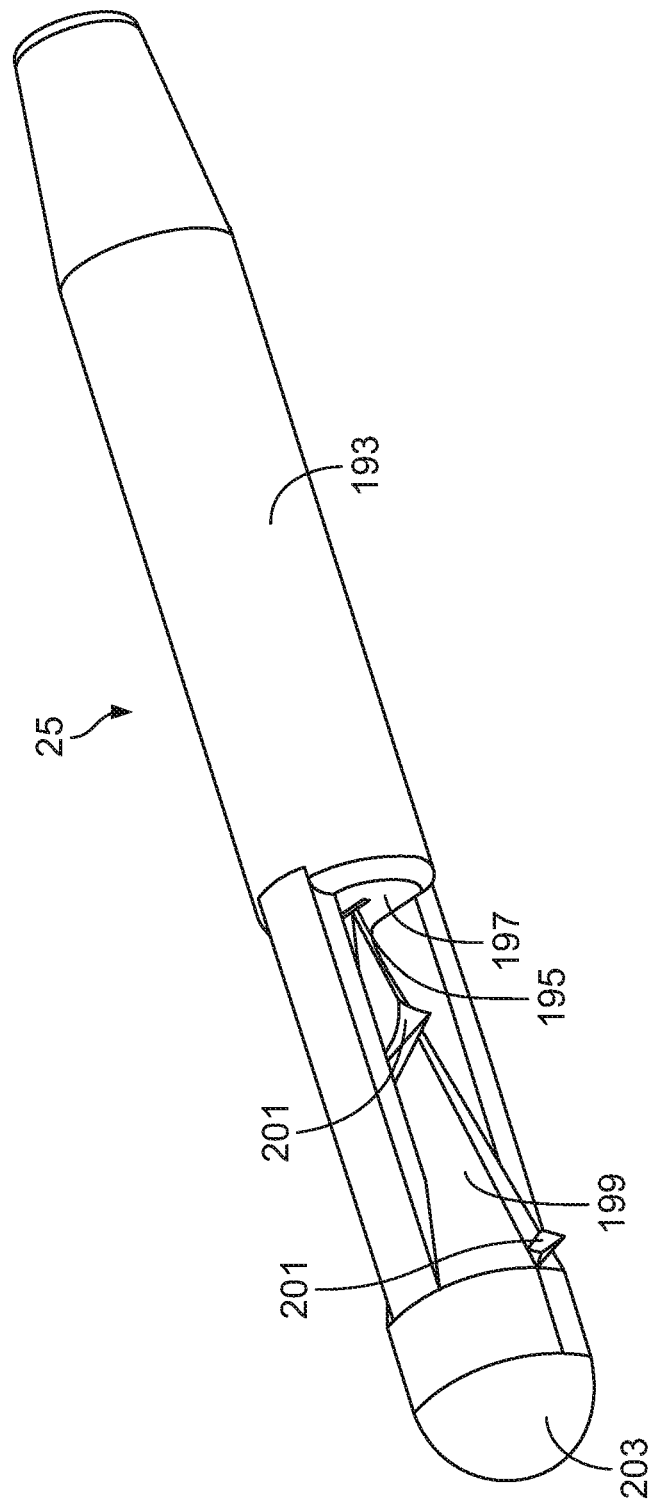

The nozzle 25 of the LTA device 10 is designed to extend past the distal end 31d of the ETT 31 and act as an outlet for local anesthetic. Angled configurations of the nozzle, between approximately 15 degrees and 90 degrees relative to the longitudinal axis of the conduit 20. This angle facilitates easier intubation, particularly since the nozzle is placed in close spatial relationship to and distal from the cuff 32. This angled and blunted configuration to the nozzle defines a combined anesthesia nozzle and ETT introducer tip. In one embodiment shown in FIG. 15A, the nozzle 25 is a tube 189 with a plurality of perforations 191 on the sides and end. In a preferred embodiment shown in FIG. 15B, the nozzle 25 is designed to produce a radial spray. The nozzle 25 features a shaft portion 193 with a slit 195 on the distal surface 197. The slit 195 is narrow relative to the shaft portion 193 such that the anesthetic is ejected at a high velocity, according to Bernoulli's principle, and disperses the liquid as a spray. Besides a slit, other openings are also suitable, including a fan-shaped, cone-shaped, and circular openings. A cone 199 deflects the mist radially, and a plurality of baffles 201 further disperses the mist.

Having the nozzle 25 extend past the distal end 31d of the ETT 31 provides several distinct advantages. First, anesthetic can be administered during the intubation procedure. Prior art devices had to be placed first before anesthetic could be delivered. Second, because the nozzle 25 is distally positioned relative to the balloon cuff 32, the risk of the anesthetic pooling above the cuff in situ is eliminated. Some prior art devices had dispersion points along the length of the ETT. While this allowed for continued administration of local anesthetic while the ETT is in place, it also meant that anesthetic was delivered above the balloon cuff. Often this anesthetic would flow down the trachea and pool at the balloon cuff. Such concentrated doses of anesthetic have been known to cause damage to the sensitive tissues of the trachea. Third, using a nozzle helps to propel and diffuse the anesthetic spray to uniformly cover a wide area. Prior art devices typically use a series of perforations to deliver the anesthetic. These may or may not produce a spray, but the reach of the spray is far less than in the present invention. Thus, the present invention is able to utilize a shorter nozzle, which avoids the difficulty of negotiating a larger feature through the structures of the airway.

In both embodiments, the nozzle 25 is preferably made of a flexible, non-rigid material so as to avoid perforation of the trachea. Preferably, the end 203 of the nozzle 25 is blunted or rounded to prevent trauma to the trachea and other structures in the throat. Further, the nozzle 25 may have a slight angle in relation to the rest of the conduit 20 to further reduce risk of tracheal perforation. This angled tip, similar to a coude tip, may also provide an anesthesiologist a slight advantage in placement of the LTA device 10 through the vocal cords in the case of a difficult intubation such as in an "anterior airway." The nozzle 25 provides tactile feedback when the nozzle 25 passes over the tracheal rings. Because of the close proximity of the trachea and esophagus, the anesthesiologist could place the ETT into the esophagus on accident. The trachea, however, contains tracheal rings, which are cartilaginous protrusions on the trachea wall, while the esophagus is smooth. Thus, if the nozzle bounces off the tracheal rings during intubation, the anesthesiologist can be assured that the proper pathway is being intubated.

The dispenser 15 and conduit 20 and nozzle 25 may be designed to be modular in function. This would allow for the dispensing portion 15 to be used with different conduits 20 and nozzles 25. For instance, a smaller conduit 20 may be necessary for use with pediatric patients. Modular design would allow the same dispenser to be used by simply switching between conduits.

Intravenous Embodiment

Figure 16:
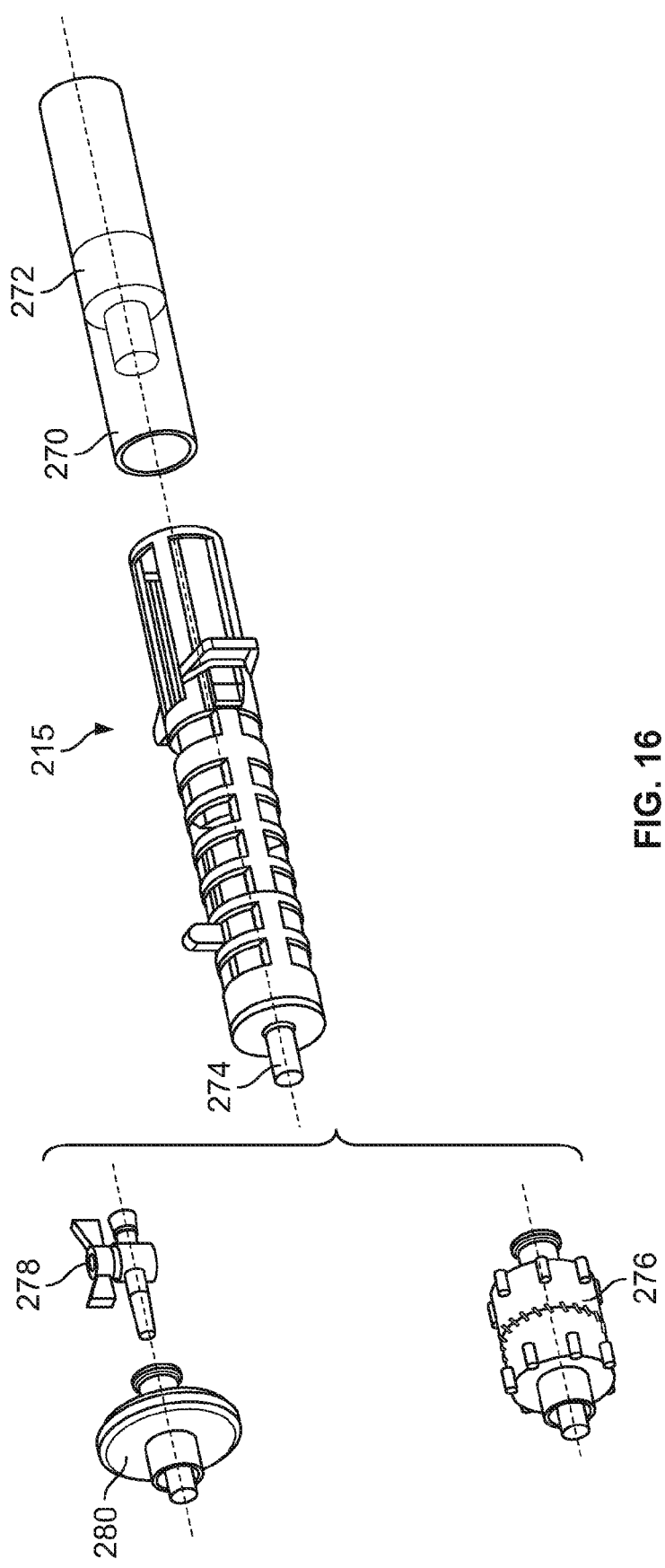
FIG. 16 is an exploded view of an intravenous dispensing device, in accordance with features of the present invention.

Many of the dispensing mechanisms discussed supra are also applicable to intravenous delivery of anesthetic or medicine. FIG. 16 depicts the intravenous embodiment of the dispenser.

The dispenser 215 is generally the same as the vial embodiment. The dispenser 215 is comprised of a housing 235 that contains a piston 260 and a needle 265. The housing 235 is adapted to receive a vial 270. The vial 270 is plugged with a stopper 272. The primary difference is the lack of a pressure release valve 80. Instead of a pressure release valve 80 in communication with an actuation means 30, the fluid channel formed by the needle terminates in luer taper 274 that engages a variable flow regulator 276 or a stopcock 278 in communication with a passive flow regulator 280. Variable flow regulators are commercially available, such as the Flow Regulator, available from Quosina Corp. (Edgewood, N.Y.). The flow regulator 276 or 280 is then placed in direct communication with intravenous tubing via luer lock or another similar adapter.

In operation, the dispenser 215 provides consistent and controlled release of anesthetic or medicine. The piston 260 in the dispenser 215 imparts continuous pressure on the fluid within the vial, forcing the fluid into the channel defined by the needle 265. Flow out of the dispenser 215 is controlled by the variable flow regulator 276 or passive flow regulator 280 which also compensates for decreasing pressure as the dispenser dispenses the medicament.

The presently invented dispenser may be used in a variety of contexts where sustained and controlled release of a fluid is required. For instance, often drugs need to be delivered to a patient slowly, but such delivery does not need to be so accurate as to require the need of a bulky intravenous pump. Additionally, some drugs are only available in vials or syringes. Previously, a doctor or nurse had to slowly administer the drug to the patient, which could take as long as ten minutes in some circumstances, and this practice produced highly inaccurate doses. The present invention allows the user to provide sustained release without requiring a person to administer the doses. Instead, the medical professional can perform other care related tasks during the injection process, such as computer charting. Advantageously, embodiments of the device contain only passive components, i.e., the components do not require electrical or mechanical input other than the force necessary to load the cartridge and set the flow rate. The passive component design improves the reliability and predictability of the device.

Figure 17A:
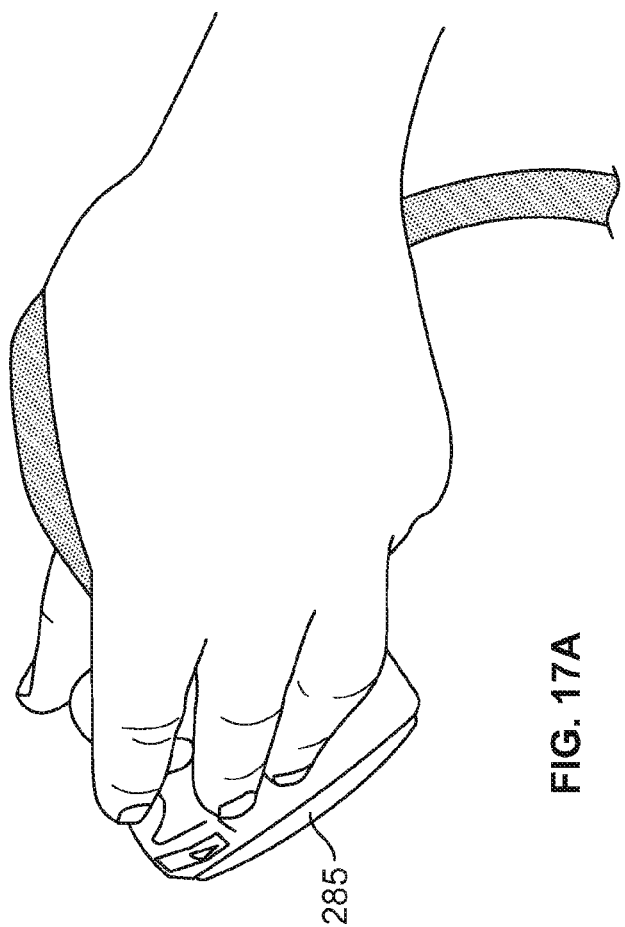
FIGS. 17A-B depict the intravenous dispensing device as applied to a nerve block procedure.
Figure 17A:
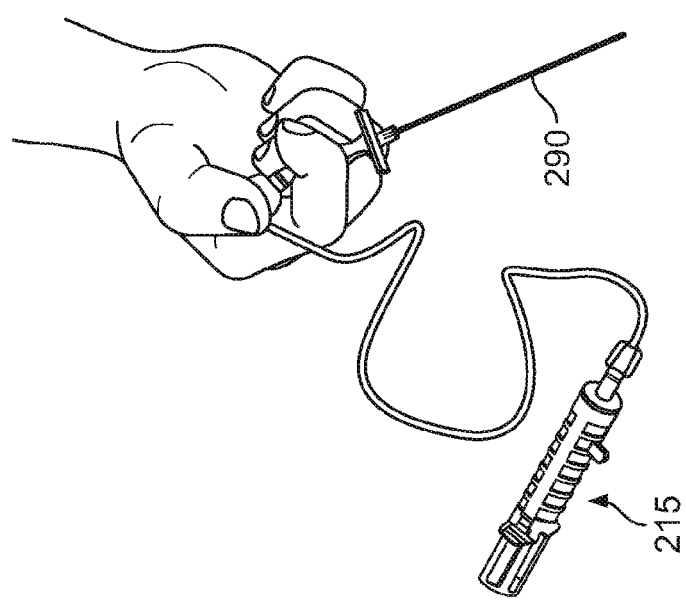

One procedure where the presently invented device can have substantial impact is in a local anesthetic nerve block procedure. During a nerve block, a doctor administers a dose of local anesthetic at or near a nerve. In order to find the proper nerve and target the dose, the doctor ultrasounds the region of the body where the nerve block is to be delivered. As depicted in FIG. 17A, one of the doctor's hands is holding the ultrasound probe 285 while the other is holding the needle 290. Previously, the needle was connected through an intravenous line to a syringe, and the doctor required an assistant to depress the plunger on the syringe to administer the dose. Now, using the invented device, the doctor can simply depress a button to deliver a dose at the right time and in the right place.

Figure 17B:
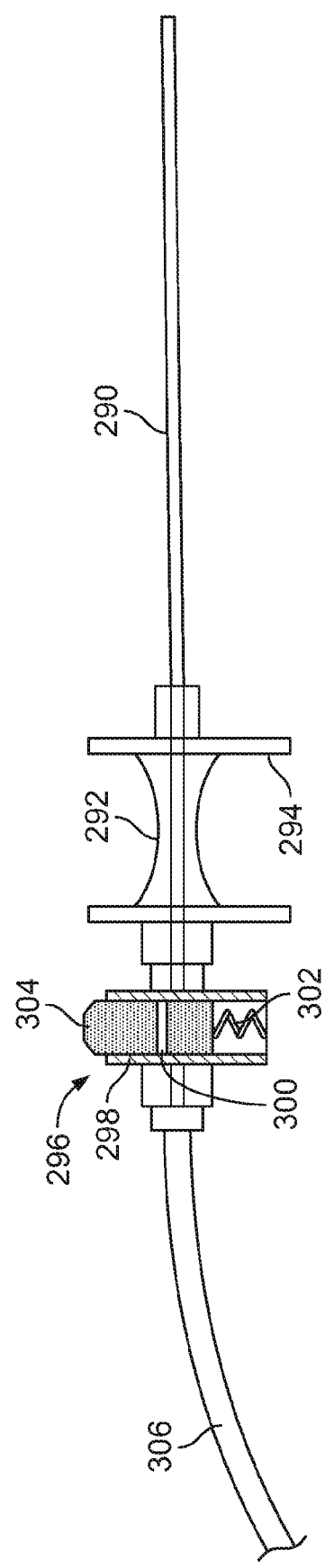

As shown in FIG. 17B, the needle 290 is connected to a handle 292, featuring a finger guard 294. The connection is a standard luer lock or luer taper connection. A valve 296 blocks fluid flow at the upstream portion of the handle 292. The valve 296 is substantially similar to the pressure relief valve 104 in that it contains a movable block 298, a through-hole 300, a spring 302, and a protrusion 304. Here, the protrusion 304 serves as a button that the anesthesiologist can depress to dispense anesthetic. Further upstream, the valve is connected to an intravenous conduit 306 via another luer lock or luer taper connection. The intravenous conduit 306 carries fluid from a dispenser 215. Optionally, a passive flow regulator 280 is placed between the dispenser 215 and the intravenous conduit 306. This arrangement provides a continuous pressurized stream of anesthetic to the needle 290, which can easily be administered by the doctor without the aid of an assistant.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting, but are instead exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the terms "comprising" and "wherein." Moreover, in the following claims, the terms "first," "second," and "third," are used merely as labels, and are not intended to impose numerical requirements on their objects. Further, the limitations of the following claims are not written in means-plus-function format and are not intended to be interpreted based on 35 U.S.C. .sctn. 112(f) unless and until such claim limitations expressly use the phrase "means for" followed by a statement of function void of further structure.

The present methods can involve any or all of the steps or conditions discussed above in various combinations, as desired. Accordingly, it will be readily apparent to the skilled artisan that in some of the disclosed methods certain steps can be deleted or additional steps performed without affecting the viability of the methods.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," "more than" and the like include the number recited and refer to ranges which can be subsequently broken down into subranges as discussed above. In the same manner, all ratios disclosed herein also include all subratios falling within the broader ratio.

One skilled in the art will also readily recognize that where members are grouped together in a common manner, such as in a Markush group, the present invention encompasses not only the entire group listed as a whole, but each member of the group individually and all possible subgroups of the main group. Accordingly, for all purposes, the present invention encompasses not only the main group, but also the main group absent one or more of the group members. The present invention also envisages the explicit exclusion of one or more of any of the group members in the claimed invention.

What is claimed is:

1. A medication delivery device, the device comprising:
   a malleable conduit comprising an upstream end and a downstream end configured to deliver medication, wherein the conduit is reversibly deformable into a shape that facilitates intubation;
   a dispenser comprising:
      a housing comprising a reservoir, a first end and a second end, the first end of the housing attached to a syringe containing a medication, the syringe further comprising a plunger and a barrel for transferring the medication from the syringe to the reservoir; and
      a releasing mechanism for releasing the medication from the reservoir;
   a pressurizing mechanism for keeping the medication pressurized within the reservoir; and
   a connector that provides fluid communication between the syringe and the upstream end of the conduit through the second end of the housing.

2. The device of claim 1, wherein the connector is a luer connector.

3. The device of claim 1, further comprising a nozzle comprising a proximal end and a distal end; wherein the proximal end of the nozzle is in fluid communication with the downstream end of the conduit wherein the distal end of the nozzle is blunted; and wherein the nozzle is configured to function as an introducer.

4. The device of claim 3, wherein the distal end of the nozzle comprises a cone having an inner surface and an outer surface; wherein the cone contains baffles on the outer surface of the cone; and wherein the nozzle ejects a high velocity stream of fluid into the inner surface of the cone.

5. The device of claim 1, wherein a substantial portion of the conduit is enclosed in an endotracheal tube.

6. The device of claim 1, wherein the pressurizing mechanism is a one-way valve located within the housing at the first end; and wherein the releasing mechanism is a pressure relief valve located within the housing at the second end.

7. The device of claim 1, wherein the pressurizing mechanism is a locking mechanism mounted on a proximal end of the barrel of the syringe.

8. The device of claim 1, wherein the releasing mechanism is a solenoid valve.

* * * * *